(12) United States Patent
Wagner et al.

(10) Patent No.: US 7,407,648 B2
(45) Date of Patent: Aug. 5, 2008

(54) MEROCYANINE DERIVATIVES FOR COSMETIC USE

(75) Inventors: Barbara Wagner, Lörrach (DE); Thomas Ehlis, Freiburg (DE); Kai Eichin, Wittlingen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 618 days.

(21) Appl. No.: 10/520,840

(22) PCT Filed: Jul. 1, 2003

(86) PCT No.: PCT/EP03/06955

§ 371 (c)(1),
(2), (4) Date: Jan. 7, 2005

(87) PCT Pub. No.: WO2004/006878

PCT Pub. Date: Jan. 22, 2004

(65) Prior Publication Data

US 2005/0255055 A1   Nov. 17, 2005

(30) Foreign Application Priority Data

Jul. 10, 2002   (EP)   .................. 02405582

(51) Int. Cl.
| | |
|---|---|
| *A61Q 17/04* | (2006.01) |
| *A61K 8/37* | (2006.01) |
| *A61K 31/21* | (2006.01) |
| *A61K 31/235* | (2006.01) |
| *A61K 31/10* | (2006.01) |
| *A61K 31/04* | (2006.01) |
| *A61K 8/04* | (2006.01) |
| *A61Q 1/10* | (2006.01) |
| *A01N 37/00* | (2006.01) |
| *A01N 31/235* | (2006.01) |
| *A01N 41/10* | (2006.01) |
| *A01N 33/24* | (2006.01) |

(52) U.S. Cl. .................. 424/59; 424/70.9; 514/506; 514/532; 514/710; 514/741

(58) Field of Classification Search .................. 424/59, 424/70; 560/12; 514/506, 532, 710, 741
See application file for complete search history.

(56) References Cited

U.S. PATENT DOCUMENTS

| | | | | |
|---|---|---|---|---|
| 3,723,154 | A | 3/1973 | Oliver | ............ 117/33.3 |
| 4,309,500 | A | 1/1982 | Shishido | ............ 430/507 |
| 4,749,643 | A | 6/1988 | Öhlschläger | ............ 430/512 |
| 5,806,834 | A | 9/1998 | Yoshida | ............ 252/589 |

FOREIGN PATENT DOCUMENTS

| | | |
|---|---|---|
| DE | 3531383 | 3/1987 |
| EP | 0127819 | 12/1984 |
| WO | 00/20388 | 4/2000 |

OTHER PUBLICATIONS

Sieber, Fritz, Dec. 1984, Proc. National Academy of Sciences, vol. 81, pp. 7584-7587.*

* cited by examiner

*Primary Examiner*—Johann Richter
*Assistant Examiner*—Andriae M Holt
(74) *Attorney, Agent, or Firm*—Kevin T. Mansfield

(57) ABSTRACT

The use is described of merocyanine derivatives of formula (1), wherein $R_1$ and $R_2$ are each independently of the other hydrogen; $C_1$-$C_{22}$alkyl; cyclo-$C_3C_8$alkyl; or unsubstituted or $C_1$-$C_5$alkyl- or $C_1$-$C_5$alkoxy-substituted $C_6$-$C_{20}$aryl; orl; or $R_1$ and $R_2$ together with the nitrogen atom linking them form a —$(CH_2)_m$— ring which is uninterrupted or, interrupted by —O— or by —NH—; $R_3$ is a cyano group; —$COOR_5$; —$CONHR_5$; —$COR_5$; or —$SO_2R_5$; $R_4$ is a cyano group; —$COOR_6$; —$CONHR_6$; —$COR_6$; or —$SO_2R_6$; $R_5$ and $R_6$ are each independently of the other $C_1$-$C_{22}$alkyl; or unsubstituted or $C_1$-$C_5$alkyl substituted $C_6$-$C_{20}$aryl; or $R_3$ and $R_4$ together or $R_5$ and $R_6$ together form in a 5- to 7-membered, monocyclic, carbocyclic or heterocyclic ring; $Z_1$, and $Z_2$ are each independently of the other a —$(CH_2)_n$— group which is uninterrupted or interrupted by —O—, —S—, or by —$NR_7$—, and/or is unsubstituted or substituted by $C_1$-$C_5$alkyl; $R_7$ is ($C_1C_5$alkyl; l is from 1 to 4; m is from 1 to 7; n is from 1 to 4; when n=2, $R_1$, $R_5$ or $R_6$ is a bivalent alkyl group; or $R_1$, and $R_2$ together with the 2 nitrogen atoms linking them form a —$(CH_2)_m$— ring; when n=3, $R_1$, $R_5$ or $R_6$ is a trivalent alkyl group; when n=4, $R_1$, $R_5$ or $R_6$ is a tetravalent alkyl group; and $R_1$, and $R_2$ in formula (1) are not simultaneously hydrogen, in protecting human and animal hair and skin from UV radiation.

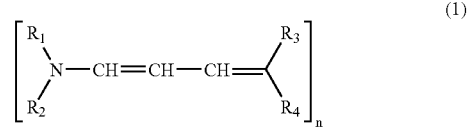

(1)

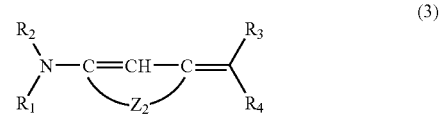

(3)

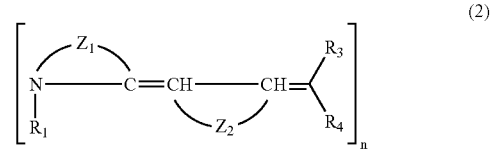

(2)

19 Claims, No Drawings

MEROCYANINE DERIVATIVES FOR COSMETIC USE

The present invention relates to the use of merocyanine derivatives in protecting human and animal hair and skin from UV radiation and to cosmetic compositions comprising such compounds.

The compounds for use in accordance with the invention correspond to formula

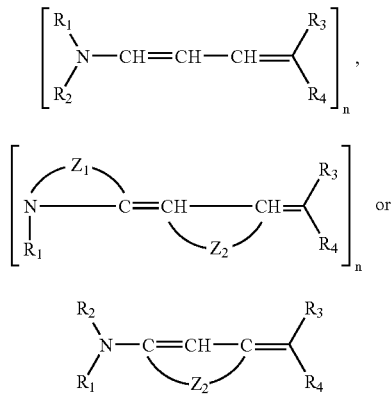

wherein
$R_1$ and $R_2$ are each independently of the other hydrogen; $C_1$-$C_{22}$alkyl; cyclo-$C_3$-$C_8$alkyl; or unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is uninterrupted or interrupted by —O— or by —NH—;
$R_3$ is a cyano group; —$COOR_5$; —$CONHR_5$; —$COR_5$; or —$SO_2R_5$; —$CONR_1R_6$;
$R_4$ is a cyano group; —$COOR_6$; —$CONHR_6$; —$COR_6$; or —$SO_2R_6$; —$CONR_2R_6$;
$R_5$ and $R_6$ are each independently of the other $C_1$-$C_{22}$alkyl; cyclo-$C_3$-$C_8$alkyl; or unsubstituted or $C_1$-C6alkyl-substituted $C_6$-$C_{20}$aryl;
or $R_3$ and $R_4$ together or $R_5$ and $R_6$ together form a 5- to 7-membered, monocyclic, carbocyclic or heterocyclic ring;
$Z_1$ and $Z_2$ are each independently of the other a —$(CH_2)_l$— group which is uninterrupted or interrupted by —O—, —S—, or by —$NR_7$—, and/or is unsubstituted or substituted by $C_1$-$C_6$alkyl;
$R_7$ is $C_1$-$C_5$alkyl;
l is from 1 to 4;
m is from 1 to 7;
n is from 1 to 4;
when n=2, $R_1$, $R_5$ or $R_6$ is a bivalent alkyl group; or $R_1$ and $R_2$ together with the 2 nitrogen atoms linking them form a —$(CH_2)_m$— ring;
when n=3, $R_1$, $R_5$ or $R_6$ is a trivalent alkyl group;
when n=4, $R_1$, $R_5$ or $R_6$ is a tetravalent alkyl group; and
$R_1$ and $R_2$ in formula (1) are not simultaneously hydrogen.

Preference is given to the use of compounds of formula (1) or (2a)

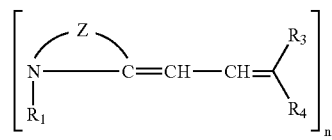

wherein
$R_1$ and $R_2$ are each independently of the other hydrogen; $C_1$-$C_{22}$alkyl; or unsubstituted or $C_1$-$C_5$alkyl- or $C_1$-$C_5$alkoxy-substituted $C_6$-$C_{20}$aryl; or $R_1$ and $R_2$ together with the nitrogen atom linking them form a —$(CH_2)_m$— ring which is uninterrupted or interrupted by —O— or by —NH—;
$R_3$ is a cyano group; —$COOR_5$; —$CONHR_5$; —$COR_5$; or —$SO_2R_5$;
$R_4$ is a cyano group; —$COOR_6$; —$CONHR_6$; —$COR_6$; or —$SO_2R_6$;
$R_5$ and $R_6$ are each independently of the other $C_1$-$C_{22}$alkyl; or unsubstituted or $C_1$-$C_5$alkyl-substituted $C_6$-$C_{20}$aryl; or $R_5$ and $R_6$ together form a 5- to 7-membered, monocyclic, carbocyclic or heterocyclic ring;
Z is a —$(CH_2)_l$— group which is uninterrupted or interrupted by —O—, —S—, or by —$NR_7$—, and/or is unsubstituted or substituted by $C_1$-$C_6$alkyl;
$R_7$ is $C_1$-$C_6$alkyl;
l is from 1 to 4;
m is from 1 to 7;
n is from 1 to 4;
when n=2, $R_1$, $R_5$ or $R_6$ is a bivalent alkyl group; or $R_1$ and $R_2$ together with the 2 nitrogen atoms linking them form a —$(CH_2)_m$— ring;
when n=3, $R_1$, $R_5$ or $R_6$ is a trivalent alkyl group;
when n=4, $R_1$, $R_5$ or $R_6$ is a tetravalent alkyl group; and
$R_1$ and $R_2$ in formula (1) are not simultaneously hydrogen.
The compounds of formula (1) may be present in the form of E,E-, E,Z- or Z,Z-isomers.

$C_1$-$C_{22}$Alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octyl-phenoxyethyl, 3-(2,4-di-tert-amylphenoxy)-propyl, ethoxycarbonylmethyl-2-(2-hydroxy-ethoxy)ethyl or 2-furylethyl.

$C_1$-$C_6$alkoxy denotes methoxy, ethoxy, n-propoxy, isopropoxy, n-butoxy, sec-butoxy, tert-butoxy, amyloxy, isoamyloxy or tert-amyloxy.

$C_8$-$C_{10}$aryl denotes, for example, phenyl, tolyl, anisyl, mesityl, chlorophenyl, 2,4-di-tert-amylphenyl and naphthyl.

Heterocyclic radicals contain one, two, three or four identical or different ring hetero atoms. Special preference is given to heterocycles which contain one, two or three, especially one or two, identical or different hetero atoms. The heterocycles may be mono- or poly-cyclic, for example mono-, bi- or tri-cyclic. They are preferably mono- or bi-cyclic, especially mono-cyclic. The rings preferably contain 5, 6 or 7 ring members. Examples of monocyclic and bicyclic heterocyclic systems from which radicals occurring in the compounds of formula (1) or (2) may be derived are, for example, pyrrole, furan, thiophene, imidazole, pyrazole, 1,2, 3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothiophene, benzofuran, pyrrolidine, piperidine, piperazine, morpholine and thiomorpholine.

When $R_5$ and $R_6$ together form a 5- to 7-membered monocyclic carbocyclic or heterocyclic ring, such a ring is, for example, a 1,3-dioxocyclohexane ring such as, for example, a dimedone ring, a 1,3-dioxo-5,5-diethylcyclohexane ring, a 1,3-diaza-2,4,6-trioxocyclohexane ring such as, for example, a barbituric acid ring, a 1,3-dimethylbarbituric acid ring, a 1-phenylbarbituric acid ring, a 1-methyl-3-octylbarbituric acid ring, a 1-ethyl-3-octyloxy-carbonylethylbarbituric acid ring, a 1,2-diaza-3,5-dioxocyclopentane ring such as, for example, a 1,2-diaza-1,2-dimethyl-3,5-dioxocyclopentane ring, a 1,2-diaza-1,2-diphenyl-3,5-dioxocyclopentane ring, or a 2,4-diaza-1-alkoxy-3,5-dioxocyclohexene ring such as, for example, a 2,4-diaza-1-ethoxy-4-ethyl-3,5-dioxocyclohexene ring, a 2,4-diaza-1-ethoxy-4-[3-(2,4-di-tert-amylphenoxy)propyl]-3,5-dioxocyclohexene ring etc.

Preference is given to the use in accordance with the invention of compounds of formula (1) or (2) wherein
$R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
$R_3$ is a cyano group; —$COOR_5$; —$CONHR_5$; —$COR_5$; or —$SO_2R_5$;
$R_4$ is a cyano group; —$COOR_6$; —$CONHR_6$; —$COR_6$; or —$SO_2R_6$;
$R_5$ and $R_6$ are each independently of the other $C_1$-$C_{22}$alkyl; or $C_6$-$C_{20}$aryl; and
Z is as defined in claim 1.

Amongst those compounds special preference is given to compounds of formula (1) or (2) wherein
$R_3$ is a cyano group; and
$R_4$ is —$CONHR_6$; and
$R_6$ is $C_1$-$C_{22}$alkyl; or $C_6$-$C_{20}$aryl,
and especially to compounds of formula (1) or (2) wherein
$R_6$ is $C_4$-$C_{20}$alkyl.

Preference is also given to compounds of formula (1) or (2) wherein
$R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
$R_3$ is —$COOR_5$;
$R_4$ is a cyano group; —$COOR_6$; or —$SO_2R_6$;
$R_5$ and $R_6$ are each independently of the other $C_1$-$C_{22}$alkyl; or $C_6$-$C_{20}$aryl; and
m is from 1 to 7.

Amongst those compounds preference is given to those wherein
$R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
$R_3$ is —$COOR_5$;
$R_4$ is —$COOR_6$;
$R_5$ and $R_6$ are each independently of the other $C_1$-$C_{22}$alkyl; or $C_6$-$C_{20}$aryl; and
m is from 1 to 7;
and to compounds of formula (1) or (2) wherein
$R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
$R_3$ is —$COOR_5$;
$R_4$ is a cyano group;
$R_5$ is $C_1$-$C_{22}$alkyl; or $C_6$-$C_{20}$aryl; and
m is from 1 to 7;
and to compounds of formula (1) or (2) wherein
$R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
$R_3$ is —$COOR_5$;
$R_4$ is —$SO_2R_6$;
$R_5$ and $R_6$ are each independently of the other $C_1$-$C_{22}$alkyl; or $C_6$-$C_{20}$aryl; and
m is from 1 to 7.

Preference is further given to the use of compounds of formula

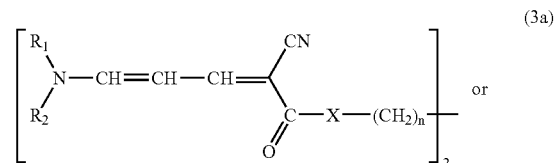

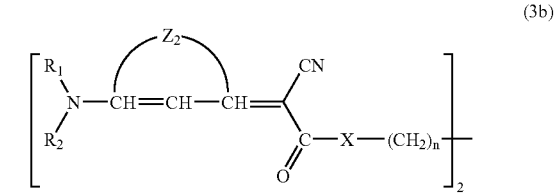

wherein
$R_1$ and $R_2$ are each independently of the other $C_0$-$C_{22}$alkyl; or $R_1$ and $R_2$ together with the 2 nitrogen atoms linking them form a —$(CH_2)_m$— ring;
X is —O—; or —NH—;
$Z_2$ a —$(CH_2)_l$— group which is uninterrupted or interrupted by —O—, —S—, or by —$NR_7$—, and/or is unsubstituted or substituted by $C_1$-$C_6$alkyl; and
n is from 1 to 3;
and especially compounds of formula (3) wherein
$R_1$ and $R_2$ are each independently of the other $C_1$-$C_{22}$alkyl; or $R_1$ and $R_2$ together with the nitrogen atom linking them form the radical

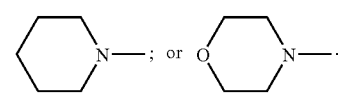

Preference is further given to the use of compounds of formula

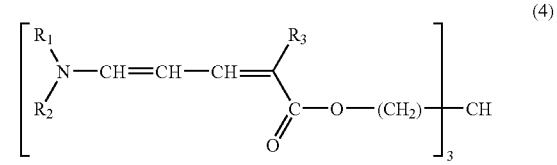

wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is a cyano group; —COOR$_5$; —CONHR$_5$; —COR$_5$; or —SO$_2$R$_5$; and $R_5$ and $R_6$ are each independently of the other $C_1$-$C_{22}$alkyl; or $C_6$-$C_{20}$aryl;

and very especially compounds of formula (4) wherein $R_1$ and $R_2$ are each independently of the other $C_1$-$C_{22}$alkyl; or $R_1$ and $R_2$ together with the nitrogen atom linking them form the radical <chemical structure: piperidine N—; or morpholine N—>

Preference is further given to the use of compounds of formula (5)

<chemical structure of formula (5)> wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is a cyano group; —COOR$_5$; —CONHR$_5$; —COR$_5$; or —SO$_2$R$_5$; and $R_5$ is $C_1$-$C_{22}$alkyl; or $C_6$-$C_{20}$aryl;

and very especially compounds of formula (4) wherein $R_1$ and $R_2$ are each independently of the other $C_1$-$C_{22}$alkyl; or $R_1$ and $R_2$ together with the nitrogen atom linking them form the radical <chemical structure: piperidine N—; or morpholine N—>

Compounds of formula (2) that are preferably used are those wherein

Z is an atom grouping which results in the formation of an oxazolidine ring, a pyrrolidine ring or a thiazolidine ring.

Amongst those compounds very special preference is given to those of formula (2a)

<chemical structure of formula (2a)> wherein $R_8$ and $R_9$ are each independently of the other hydrogen; or $C_1$-$C_5$alkyl; and Y is —O—; —S—; or —CH$_2$—;

and $R_1$, $R_3$, $R_4$ and n are as defined in claim 1.

Special preference is given to compounds of formula (2a) wherein $R_1$ is $C_1$-$C_{12}$alkyl;

$R_3$ is a cyano group; —COOR$_5$; —CO R$_5$; or —SO$_2$R$_5$;

$R_4$ is —COR$_6$; or —COOR$_6$; and $R_5$ and $R_6$ are each independently of the other unsubstituted or $C_1$-$C_5$alkyl- or $C_1$-$C_5$alkoxy-substituted $C_6$-$C_{20}$aryl.

Further compounds for use in accordance with the invention are listed in Table MC1 hereinbelow:

TABLE MC1

| Compound of formula | Structure | $\lambda_{max}$ [nm] |
|---|---|---|
| MC01 | <structure with oxazolidine, SO$_2$-phenyl, COOC$_6$H$_{13}$-(n)> | 362 (MeOH) |
| MC02 | <structure with oxazolidine, CN, COOC$_{12}$H$_{25}$-(n)> | 374 (MeOH) |
| MC03 | <structure with oxazolidine, C$_{12}$H$_{25}$-(n), CN, CN> | 372 (MeOH) |

TABLE MC1-continued

| Compound of formula | Structure | $\lambda_{max}$ [nm] |
|---|---|---|
| MC04 | 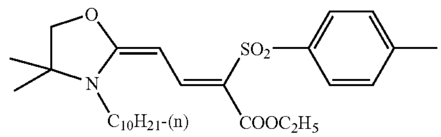 | 361 (MeOH) |
| MC05 | 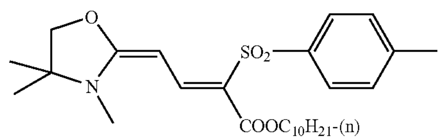 | 362 (MeOH) |
| MC06 | 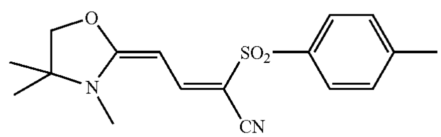 | 374 (MeOH) |
| MC07 | 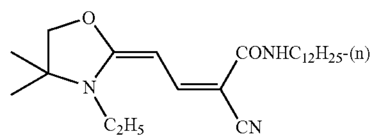 | 375 (EtOH) |
| MC08 | 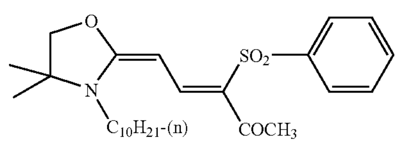 | 373 (MeOH) |
| MC09 | 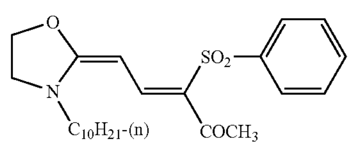 | 370 (MeOH) |
| MC10 | 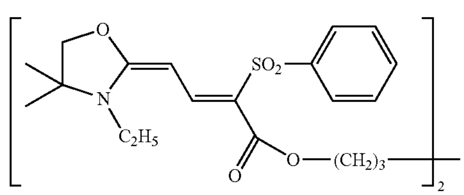 | 362 (MeOH) |
| MC11 | 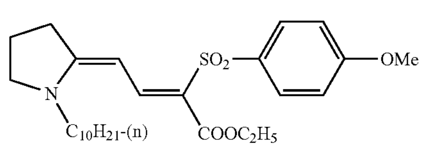 | 375 (MeOH) |
| MC12 | 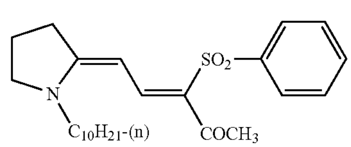 | 392 (MeOH) |

TABLE MC1-continued

| Compound of formula | Structure | $\lambda_{max}$ [nm] |
|---|---|---|
| MC13 | 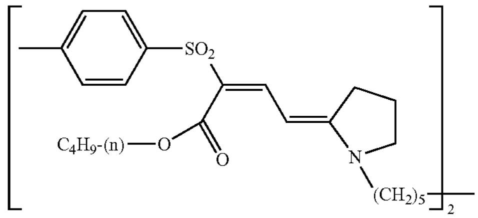 | 380 (MeOH) |
| MC14 | 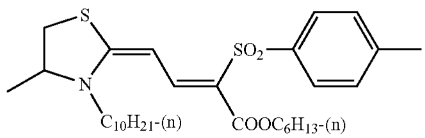 | 392 (MeOH) |
| MC15 | 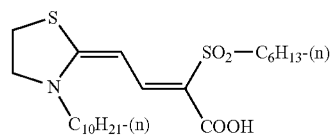 | 384 (MeOH) |
| MC16 | 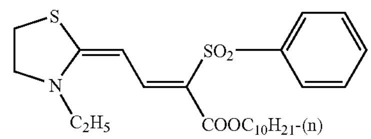 | 390 (MeOH) |
| MC17 | 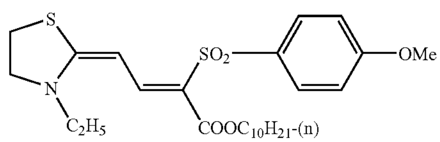 | 385 (MeOH) |
| MC18 | 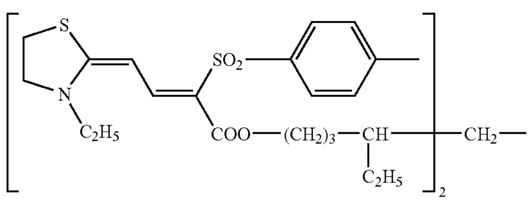 | 384 (MeOH) |
| MC19 | 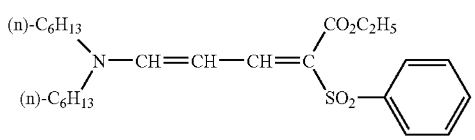 | 373 (MeOH) |
| MC20 | 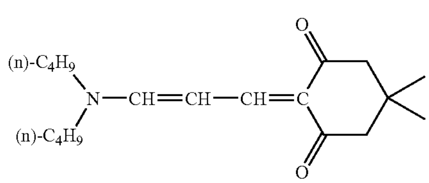 | 389 (MeOH) |
| MC21 | 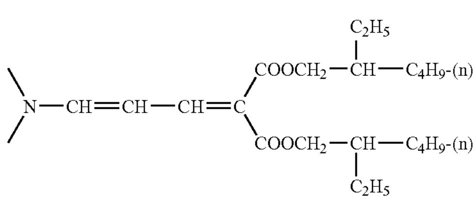 | 374 (MeOH) |

TABLE MC1-continued

| Compound of formula | Structure | $\lambda_{max}$ [nm] |
|---|---|---|
| MC22 | (n)-C$_6$H$_{13}$\N—CH=CH—CH=C(COCH$_3$)(COCH$_3$), (n)-C$_6$H$_{13}$/ | 395 (MeOH) |
| MC23 | (n)-C$_6$H$_{13}$\N—CH=CH—CH=C(CN)(CN), (n)-C$_6$H$_{13}$/ | 378 (EtOH) |
| MC24 | (n)-C$_6$H$_{13}$\N—CH=CH—CH=C(N,N'-dimethylbarbiturate), (n)-C$_6$H$_{13}$/ | 388 (MeOH) |
| MC25 | piperidino—CH=CH—CH=C(CO$_2$CH$_2$CH(C$_2$H$_5$)C$_4$H$_9$)(COCH$_3$) | 395 (MeOH) |
| MC26 | (n)-C$_6$H$_{13}$\N—CH=CH—CH=C(CO$_2$CH$_2$CH$_2$—O—C$_6$H$_3$(C$_5$H$_{11}$-t)$_2$)(SO$_2$—C$_6$H$_4$—CH$_3$), (n)-C$_6$H$_{13}$/ | 374 (MeOH) |
| MC27 | (n)-C$_4$H$_9$\N—CH=CH—CH=C(COCH$_3$)(SO$_2$—C$_6$H$_4$—CH$_3$), (n)-C$_4$H$_9$/ | 385 (MeOH) |
| MC28 | (n)-C$_4$H$_9$\N—CH=CH—CH=C(CO$_2$CH$_3$)(SO$_2$—C$_6$H$_4$—C(CH$_3$)$_3$), (n)-C$_4$H$_9$/ | 373 (MeOH) |
| MC29 | morpholino—CH=CH—CH=C(COCH$_3$)(SO$_2$—C$_6$H$_5$) | 383 (MeOH) |
| MC30 | (n)-C$_6$H$_{13}$\N—CH=CH—CH=C(COCH$_3$)(SO$_2$—C$_6$H$_5$), (n)-C$_6$H$_{13}$/ | 385 (MeOH) |
| MC31 | H$_3$C\N—CH=CH—CH=C(COCH$_3$)(CO$_2$C$_{10}$H$_{21}$-n), H$_3$C/ | 394 (MeOH) |

TABLE MC1-continued

| Compound of formula | Structure | $\lambda_{max}$ [nm] |
|---|---|---|
| MC32 | (n)-C$_6$H$_{13}$–N(–(n)-C$_6$H$_{13}$)–CH=CH–C=C(pyrazolidine-3,5-dione, 1,2-dimethyl) | 387 (MeOH) |
| MC33 | PhCH$_2$CH$_2$–N(–(n)-C$_{16}$H$_{33}$)–CH=CH–CH=C(CO$_2$C$_4$H$_9$-(n))(SO$_2$–C$_6$H$_4$–OMe) | 375 (MeOH) |
| MC34 | (4-MeC$_6$H$_4$)SO$_2$–C(=CH–CH=CH–N)(COCH$_3$)—piperazine—N–CH=CH–CH=C(COCH$_3$)(SO$_2$–C$_6$H$_4$–4-Me) | 383 (MeOH) |
| MC35 | [(n)-C$_8$H$_{17}$)$_2$N–CH=CH–CH=C(COO(CH$_2$)$_3$–)(SO$_2$Ph)]$_2$ | 374 (MeOH) |
| MC36 | [4-(–)C$_6$H$_4$–SO$_2$–C(COCH$_3$)=CH–CH=CH–N(C$_2$H$_5$)((CH$_2$)$_5$–)]$_2$ | 385 (MeOH) |
| MC37 | (H$_5$C$_2$)$_2$N–CH=CH–CH=C(COOC$_{12}$H$_{25}$-(n))(SO$_2$Ph) | 372 (MeOH) |
| MC38 | ((n)-C$_4$H$_9$)$_2$N–CH=CH–CH=C(COOC$_{14}$H$_{29}$-(n))(SO$_2$Ph) | 372 (MeOH) |
| MC39 | (H$_5$C$_2$)$_2$N–CH=CH–CH=C(CN)–C(=O)–O–CH$_2$CH(C$_2$H$_5$)C$_4$H$_9$ | 380 (EtOH) |
| MC40 | (CH$_3$)$_2$N–CH=CH–CH=C(CN)–C(=O)–O–CH$_2$CH(C$_2$H$_5$)C$_4$H$_9$ | |

Further Merocyanine Derivatives for use in Accordance with the Invention are Listed in Table MC2:

TABLE MC2a $$* \longrightarrow R_1\!\!\diagdown\!\!N\!-\!CH\!=\!CH\!-\!CH\!=\!\!\!\diagup\!\!R_3$$
$$** \longrightarrow R_2\!\!\diagup\qquad\qquad\qquad\diagdown\!\!R_4$$

| | R₁ | R₂ | R₃ | R₄ |
|---|---|---|---|---|
| MC41 | $C_2H_5$ | $C_2H_5$ | —$COOC_6H_{13}$-(n) | $COOC_6H_{13}$-(n) |
| MC42 | $C_2H_5$ | $C_2H_5$ | $COOC_8H_{17}$-(n) | $COOC_8H_{17}$-(n) |
| MC43 | $C_2H_5$ | $C_2H_5$ | $COOC_8H_{17}$-(i) | $COOC_8H_{17}$-(i) |
| MC44 | $C_2H_5$ | $C_2H_5$ | $COOC_8H_{17}$-(i) | CN |
| MC45 | $C_2H_5$ | $C_2H_5$ | $COOC_8H_{17}$-(n) | CN |
| MC46 | $C_2H_5$ | $C_2H_5$ | $COOC_{10}H_{21}$-(n) | CN |
| MC47 | $C_2H_5$ | $C_2H_5$ | $COOC_{10}H_{21}$-(n) | $SO_2C_6H_6$ |
| MC48 | $C_2H_5$ | $C_2H_5$ | $COOC_{12}H_{25}$-(n) | CN |
| MC49 | $C_2H_5$ | $C_2H_5$ | $COOC_{12}H_{25}$-(n) | $SO_2C_6H_6$ |
| MC50 | $C_2H_5$ | $C_2H_5$ | CN | $CONHC_8H_{17}$-(n) |
| MC51 | $C_2H_5$ | $C_2H_5$ | CN | $CONHC_8H_{17}$-(i) |
| MC52 | $C_2H_5$ | $C_2H_5$ | CN | $CONHC_{10}H_{21}$-(n) |
| MC53 | $C_2H_5$ | $C_2H_5$ | CN | $CONHC_{12}H_{25}$-(n) |
| MC54 | $C_4H_9$-(n) | $C_4H_9$-(n) | $COOC_4H_9$-(n) | $COOC_4H_9$-(n) |
| MC55 | $C_4H_9$-(n) | $C_4H_9$-(n) | $COOC_6H_{13}$-(n) | $COOC_6H_{13}$-(n) |
| MC56 | $C_4H_9$-(n) | $C_4H_9$-(n) | $COOC_6H_{13}$-(n) | CN |
| MC57 | $C_4H_9$-(n) | $C_4H_9$-(n) | $COOC_6H_{13}$-(n) | $SO_2C_6H_6$ |
| MC58 | $C_4H_9$-(n) | $C_4H_9$-(n) | $COOC_8H_{17}$-(n) | $COOC_8H_{17}$-(n) |
| MC59 | $C_4H_9$-(n) | $C_4H_9$-(n) | $COOC_8H_{17}$-(n) | CN |
| MC60 | $C_4H_9$-(n) | $C_4H_9$-(n) | $COOC_8H_{17}$-(n) | $SO_2C_6H_6$ |
| MC61 | $C_4H_9$-(n) | $C_4H_9$-(n) | $COOC_8H_{17}$-(i) | $COOC_8H_{17}$-(i) |
| MC62 | $C_4H_9$-(n) | $C_4H_9$-(n) | $COOC_8H_{17}$-(i) | CN |
| MC63 | $C_4H_9$-(n) | $C_4H_9$-(n) | $COOC_8H_{17}$-(i) | $SO_2C_6H_8$ |
| MC64 | $C_4H_9$-(n) | $C_4H_9$-(n) | $COOC_{10}H_{21}$-(n) | CN |
| MC65 | $C_4H_9$-(n) | $C_4H_9$-(n) | $COOC_{10}H_{21}$-(n) | $SO_2C_6H_6$ |
| MC66 | $C_4H_9$-(n) | $C_4H_9$-(n) | $COOC_{12}H_{25}$-(n) | CN |
| MC67 | $C_4H_9$-(n) | $C_4H_9$-(n) | $COOC_{12}H_{25}$-(n) | $SO_2C_6H_6$ |
| MC68 | $C_4H_9$-(n) | $C_4H_9$-(n) | CN | $CONHC_6H_{13}$-(n) |
| MC69 | $C_4H_9$-(n) | $C_4H_9$-(n) | CN | $CONHC_8H_{17}$-(n) |
| MC70 | $C_4H_9$-(n) | $C_4H_9$-(n) | CN | $CONHC_8H_{17}$-(n) |
| MC71 | $C_4H_9$-(n) | $C_4H_9$-(n) | CN | $CONHC_{10}H_{21}$-(n) |
| MC72 | $C_4H_9$-(n) | $C_4H_9$-(n) | CN | $CONHC_{12}H_{25}$-(n) |
| MC73 | $C_8H_{17}$-(i) | $C_8H_{17}$-(i) | $COOC_4H_9$-(n) | $COOC_4H_9$-(n) |
| MC74 | $C_8H_{17}$-(i) | $C_8H_{17}$-(i) | $COOC_4H_9$-(n) | CN |
| MC75 | $C_8H_{17}$-(i) | $C_8H_{17}$-(i) | $COOC_4H_9$-(n) | $SO_2C_6H_6$ |
| MC76 | $C_8H_{17}$-(i) | $C_8H_{17}$-(i) | $COOC_6H_{13}$-(n) | CN |
| MC77 | $C_8H_{17}$-(i) | $C_8H_{17}$-(i) | $COOC_6H_{13}$-(n) | $SO_2C_6H_6$ |
| MC78 | $C_8H_{17}$-(i) | $C_8H_{17}$-(i) | $COOC_8H_{17}$-(n) | CN |
| MC79 | $C_8H_{17}$-(i) | $C_8H_{17}$-(i) | $COOC_8H_{17}$-(n) | $SO_2C_6H_6$ |
| MC80 | $C_8H_{17}$-(i) | $C_8H_{17}$-(i) | $COOC_8H_{17}$-(i) | CN |
| MC81 | $C_8H_{17}$-(i) | $C_8H_{17}$-(i) | $COOC_8H_{17}$-(i) | $SO_2C_6H_6$ |
| MC82 | $C_8H_{17}$-(i) | $C_8H_{17}$-(i) | CN | $CONHC_6H_{13}$-(n) |
| MC83 | $C_8H_{17}$-(i) | $C_8H_{17}$-(i) | CN | $CONHC_8H_{17}$-(n) |
| MC84 | \[cyclohexyl ring, ** *\] | | $COOC_4H_9$-(n) | $COOC_4H_9$-(n) |
| MC85 | | | $COOC_6H_{13}$-(n) | $COOC_6H_{13}$-(n) |
| MC86 | | | $COOC_8H_{17}$-(n) | $COOC_8H_{17}$-(n) |
| MC87 | | | $COOC_8H_{17}$-(n) | CN |
| MC88 | | | $COOC_8H_{17}$-(n) | $SO_2C_6H_6$ |
| MC89 | | | $COOC_8H_{17}$-(i) | $COOC_8H_{17}$-n |
| MC90 | | | $COOC_8H_{17}$-(i) | CN |
| MC91 | | | $COOC_8H_{17}$-(i) | $SO_2C_6H_6$ |
| MC92 | | | $COOC_{10}H_{21}$-(n) | CN |
| MC93 | \[cycloheptyl ring, ** *\] | | $COOC_{10}H_{21}$-(n) | $SO_2C_6H_6$ |
| MC94 | | | $COOC_{12}H_{25}$-(n) | CN |
| MC95 | | | $COOC_{12}H_{25}$-(n) | $SO_2C_6H_6$ |
| MC96 | | | CN | $CONHC_6H_{13}$-(n) |
| MC97 | | | CN | $CONHC_8H_{17}$-(n) |
| MC98 | | | CN | $CONHC_8H_{17}$-(i) |
| MC99 | | | CN | $CONHC_{10}H_{21}$-(n) |
| MC100 | | | CN | $CONHC_{12}H_{25}$-(n) |
| MC101 | | | CN | $CONHC_{18}H_{37}$-(n) |

TABLE MC2a-continued $$* \longrightarrow R_1\!\!\diagdown\!\!N\!-\!CH\!=\!CH\!-\!CH\!=\!\!\!\diagup\!\!R_3$$
$$** \longrightarrow R_2\!\!\diagup\qquad\qquad\qquad\diagdown\!\!R_4$$

| | R₁ | R₂ | R₃ | R₄ |
|---|---|---|---|---|
| MC102 | \[oxepane ring, * **\] | | $COOC_4H_9$-(n) | $COOC_4H_9$-(n) |
| MC103 | | | $COOC_6H_{13}$-(n) | $COOC_6H_{13}$-(n) |
| MC104 | | | $COOC_8H_{17}$-(n) | $COOC_8H_{17}$-(n) |
| MC105 | | | $COOC_8H_{17}$-(n) | CN |
| MC106 | | | $COOC_8H_{17}$-(n) | $SO_2C_6H_6$ |
| MC107 | | | $COOC_8H_{17}$-(i) | $COOC_8H_{17}$-(i) |
| MC108 | | | $COOC_8H_{17}$-(i) | CN |
| MC109 | | | $COOC_8H_{17}$-(i) | $SO_2C_6H_6$ |
| MC110 | | | $COOC_{10}H_{21}$-(n) | CN |
| MC111 | | | $COOC_{10}H_{21}$-(n) | $SO_2C_6H_6$ |
| MC112 | | | $COOC_{12}H_{25}$-(n) | CN |
| MC113 | | | $COOC_{12}H_{25}$-(n) | $SO_2C_6H_6$ |
| MC114 | | | CN | $CONHC_6H_{13}$-(n) |
| MC115 | | | CN | $CONHC_8H_{17}$-(n) |
| MC116 | | | CN | $CONHC_8H_{17}$-(i) |
| MC117 | | | CN | $CONHC_{10}H_{21}$-(n) |
| MC118 | | | CN | $CONHC_{12}H_{25}$-(n) |
| MC119 | | | CN | $CONHC_{18}H_{37}$-(n) |
| MC120 | | | | |

TABLE MC2b $$\left[ * \longrightarrow R_1\!\!\diagdown\!\!N\!-\!CH\!=\!CH\!-\!CH\!=\!C(CN)\!-\!C(=\!O)\!-\!X\!-\!(CH_2)_n\!-\!*\right]_2$$
$$** \longrightarrow R_2\!\!\diagup$$

| | R₁ | R₂ | X | n |
|---|---|---|---|---|
| MC121 | $C_2H_5$ | $C_2H_5$ | O | 1 |
| MC122 | $C_2H_5$ | $C_2H_5$ | O | 2 |
| MC123 | $C_2H_5$ | $C_2H_5$ | O | 3 |
| MC124 | $C_2H_5$ | $C_2H_5$ | NH | 1 |
| MC125 | $C_2H_5$ | $C_2H_5$ | NH | 2 |
| MC126 | $C_2H_5$ | $C_2H_5$ | NH | 3 |
| MC127 | $C_4H_9$-(n) | $C_4H_9$-(n) | O | 1 |
| MC128 | $C_4H_9$-(n) | $C_4H_9$-(n) | O | 2 |
| MC129 | $C_4H_9$-(n) | $C_4H_9$-(n) | O | 3 |
| MC130 | $C_4H_9$-(n) | $C_4H_9$-(n) | NH | 1 |
| MC131 | $C_4H_9$-(n) | $C_4H_9$-(n) | NH | 2 |
| MC132 | $C_4H_9$-(n) | $C_4H_9$-(n) | NH | 3 |
| MC133 | $C_8H_{17}$-(i) | $C_8H_{17}$-(i) | O | 1 |
| MC134 | $C_8H_{17}$-(i) | $C_8H_{17}$-(i) | O | 2 |
| MC135 | $C_8H_{17}$-(i) | $C_8H_{17}$-(i) | O | 3 |
| MC136 | $C_8H_{17}$-(i) | $C_8H_{17}$-(i) | NH | 1 |
| MC137 | $C_8H_{17}$-(i) | $C_8H_{17}$-(i) | NH | 2 |
| MC138 | $C_8H_{17}$-(i) | $C_8H_{17}$-(i) | NH | 3 |
| MC139 | \[cyclohexyl ring, ** *\] | | O | 1 |
| MC140 | | | O | 2 |
| MC141 | | | O | 3 |
| MC142 | | | NH | 1 |
| MC143 | | | NH | 2 |
| MC144 | | | NH | 3 |
| MC145 | \[oxepane ring, * **\] | | O | 1 |
| MC146 | | | O | 2 |
| MC147 | | | O | 3 |
| MC148 | | | NH | 1 |
| MC149 | | | NH | 2 |
| MC150 | | | NH | 3 |

TABLE MC2c

[Structure: * → R₁-N, ** → R₂-N, connected to CH=CH-CH=C(R₃)-C(=O)-O-(CH₂)₃-CH]

| Compound | R₁ | R₂ | R₃ |
|---|---|---|---|
| MC151 | | | |
| MC152 | $C_2H_5$ | $C_2H_5$ | CN |
| MC153 | $C_2H_5$ | $C_2H_5$ | $SO_2C_6H_6$ |
| MC154 | $C_4H_9$-(n) | $C_4H_9$-(n) | CN |
| MC155 | $C_4H_9$-(n) | $C_4H_9$-(n) | $SO_2C_6H_6$ |
| MC156 | $C_8H_{17}$-(i) | $C_8H_{17}$-(i) | CN |
| MC157 | $C_8H_{17}$-(i) | $C_8H_{17}$-(i) | $SO_2C_6H_6$ |
| MC158 | (cycloheptane, ** *) | | CN |
| MC159 | (cycloheptane, ** *) | | $SO_2C_6H_6$ |
| MC160 | (oxepane, * **) | | CN |
| MC161 | (oxepane, * **) | | $SO_2C_6H_6$ |

TABLE MC2d

[Structure: * → R₁-N, ** → R₂-N, connected to CH=CH-CH=C(R₃)-C(=O)-O-(CH₂)₄-C]

| Compound | R₁ | R₂ | R₃ |
|---|---|---|---|
| MC162 | $C_2H_5$ | $C_2H_5$ | CN |
| MC163 | $C_2H_5$ | $C_2H_5$ | $SO_2C_6H_6$ |
| MC164 | $C_4H_9$-(n) | $C_4H_9$-(n) | CN |
| MC165 | $C_4H_9$-(n) | $C_4H_9$-(n) | $SO_2C_6H_6$ |
| MC166 | $C_8H_{17}$-(i) | $C_8H_{17}$-(i) | CN |
| MC167 | $C_8H_{17}$-(i) | $C_8H_{17}$-(i) | $SO_2C_6H_6$ |
| MC168 | (cycloheptane, ** *) | | CN |
| MC169 | (cycloheptane, ** *) | | $SO_2C_6H_6$ |
| MC170 | (oxepane, * **) | | CN |
| MC171 | (oxepane, * **) | | $SO_2O_6H_6$ |

TABLE MC2e

| Compound | Structure |
|---|---|
| MC172 | [Phenylsulfonyl-substituted dienamine with n-octyl ester] |
| MC173 | [Bis(cyanodienoate) linked by N,N'-diethyl-propylenediamine, with 2-ethylhexyl esters] |

TABLE MC2e-continued

| Compound | Structure |
|---|---|
| MC174 | 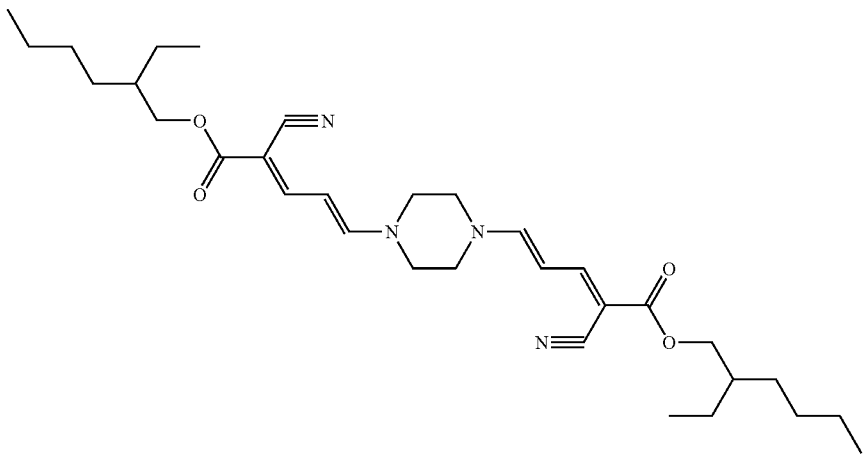 |
| MC175 | 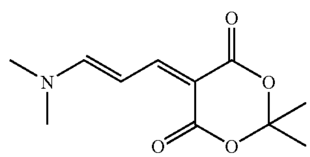 |
| MC176 | 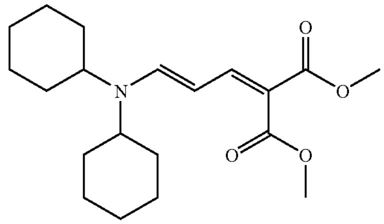 |
| MC177 | 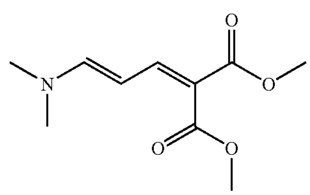 |
| MC178 | 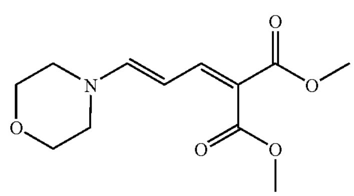 |
| MC179 | 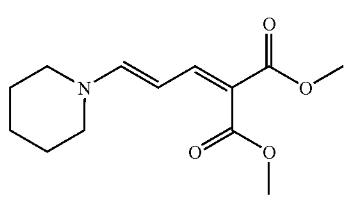 |

TABLE MC2e-continued

| Compound | Structure |
|---|---|
| MC180 | 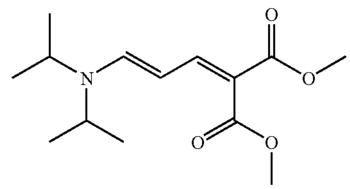 |
| MC181 | 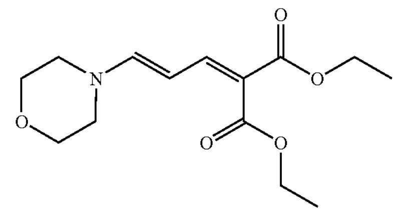 |
| MC182 | 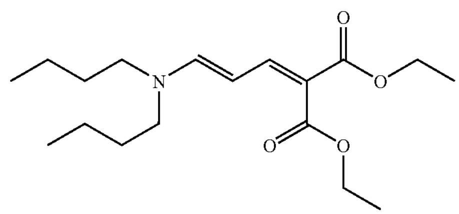 |
| MC183 | 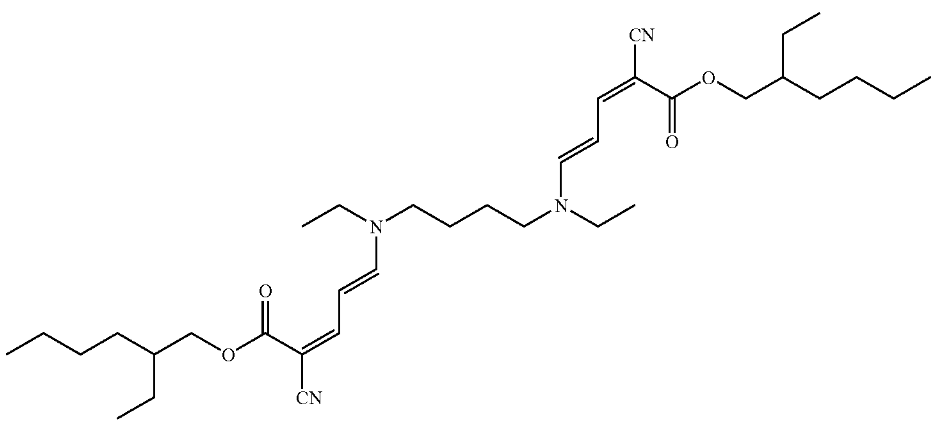 |
| MC184 | 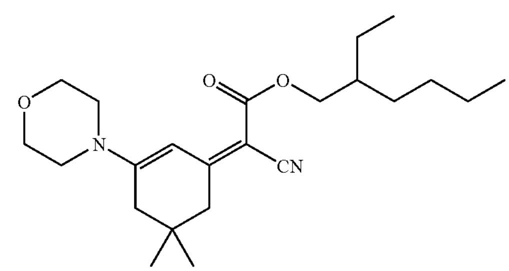 |
| MC185 | 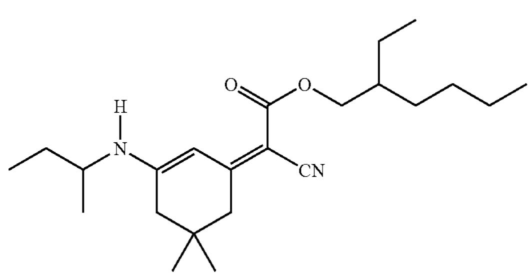 |

TABLE MC2e-continued

| Compound | Structure |
|---|---|
| MC186 | (structure shown) |

The spectroscopic data of a number of selected compounds according to the invention are listed in Table MC3:

TABLE MC3

Spectroscopic data of a number of selected compounds according to the invention

| Compound of formula | MW | $\lambda_{max}$ | $\epsilon$ | E (1%, 1 cm) |
|---|---|---|---|---|
| MC07 | 403.61 | 375 | 66 987 | 1660 |
| MC37 | 477.71 | 371 | 70 217 | 1564 |
| MC172 | 421.60 | 371 | 72 697 | 1724 |
| MC39 | 306.45 | 380 | 62 423 | 2037 |
| MC173 | 596.86 | 390 | 92 208 | 1545 |
| MC23 | 287.45 | 378 | 60 076 | 2090 |
| MC174 | 552.76 | 398 | 146 379 | 2650 |
| MC187 | 318.46 | 382 | 65 495 | 2057 |
| MC116 | 320.44 | 381 | 62 217 | 1942 |
| MC175 | 225.25 | 383 | 68 073 | 3022 |
| MC177 | 213.24 | 373 | 53 060 | 2488 |
| MC178 | 255.27 | 373 | 37 684 | 1476 |
| MC179 | 253.30 | 377 | 49 461 | 1953 |
| MC180 | 269.34 | 378 | 56 849 | 2111 |
| MC181 | 283.33 | 371 | 47 704 | 1684 |
| MC182 | 325.45 | 377 | 60 559 | 1423 |
| MC183 | 610.89 | 386 370 (sh) | 110 883 | 2570 |
| MC184 | 388.56 | 399 (acetonitrile) | | |
| MC185 | 374.57 | 388 368 (sh) (acetonitrile) | | |
| MC186 | 351.45 | 376 (acetonitrile) | | |

The merocyanine compounds of formula (1) or (2) used in accordance with the invention are, in some cases, known compounds but also include novel compounds.

The novel compounds correspond to formula

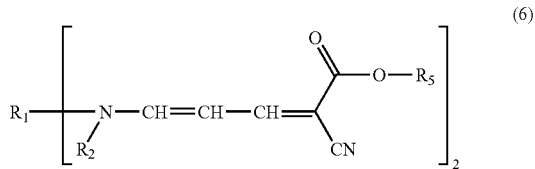

(6)

wherein
$R_1$ is $C_1$-$C_4$alkylene;
$R_2$ is $C_1$-$C_5$alkyl; or $R_1$ and $R_2$ together with the 2 nitrogen atoms linking them form a —$(CH_2)_m$— ring;
$R_5$ is $C_1$-$C_{22}$alkyl; and
m is from 1 to 7.

The UV absorbers according to the present invention can be used either in the dissolved state (soluble organic filters, solubilised organic filters) or in the micronised state (nanoscalar organic filters, particulate organic filters, UV-absorber pigments).

Any known process suitable for the preparation of microparticles can be used for the preparation of the micronised UV absorbers, for example:

wet-milling (low-viscosity micronisation process for pumpable dispersions), with a hard grinding medium, for example zirconium silicate balls in a ball mill, and a protective surfactant or a protective polymer in water or in a suitable organic solvent;

wet-kneading (high-viscosity micronisation process for non-pumpable pastes) using a continuous or discontinuous (batch) kneader. For a wet-kneading process, a solvent (water or cosmetically acceptable oils), a grinding aid (surfactant, emulsifier) and a polymeric grinding aid may be used.

Both processes may be used preferably.

spray-drying from a suitable solvent, for example aqueous suspensions or suspensions containing organic solvents, or true solutions in water, ethanol, dichloroethane, toluene or N-methylpyrrolidone etc.

by expansion according to the RESS process (Rapid Expansion of Supercritical Solutions) of supercritical fluids (e.g. $CO_2$) in which the UV filter or filters is/are dissolved, or the expansion of liquid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. Even more preferable mills are modern ball mills; manufacturers of these types of mill are, for example, Netzsch (LMZ mill), Drais (DCP-Viscoflow or Cosmo), Buhler AG (centrifugal mills) or Bachhofer. The grinding is preferably carried out with a grinding aid.

Examples of kneading apparatus for the preparation of the micronised organic UV absorbers are typical sigma-blade batch kneaders but also serial batch kneaders (IKA-Werke) or continuous kneaders (Continua from Werner und Pfleiderer).

Useful low molecular weight grinding aids for all the above micronisation processes are surfactants and emulsifiers as disclosed below in the sections entitled "Emulsifiers", "Surfactants" and "Fatty alcohols".

Useful polymeric grinding aids for water dispersion are cosmetically acceptable water-soluble polymers with Mn>500 g/mol, for example: acrylates (Salcare types), modified or non-modified polysaccharides, polyglucosides or xanthan gum. Furthermore an alkylated vinyl-pyrrolidone polymer, a vinylpyrrolidone/vinyl acetate copolymer, an acyl glutamate, an alkyl polyglucoside, Ceteareth-25 or a phospholipid may be used. Oil dispersions may comprise cosmetically acceptable waxy polymers or natural waxes as polymeric grinding aid to adjust the viscosity during and after processing. Examples of other useful polymeric grinding aids are disclosed below in the section entitled "Polymers".

Useful solvents are water, brine, (poly-)ethylene glycol, glycerol or cosmetically acceptable oils. Other useful solvents are disclosed below in the sections entitled "Esters of fatty acids", "Natural and synthetic triglycerides, including glyceryl esters and derivatives", "Pearlescent waxes", "Hydrocarbon oils" and "Silicones or siloxanes".

The micronised UV absorbers so obtained usually have an average particle size from 0.02 to 2 micrometres, preferably from 0.03 to 1.5 micrometres and more especially from 0.05 to 1.0 micrometres.

The UV absorbers according to the present invention can also be used dry in powder form. For that purpose, the UV absorbers are subjected to known grinding methods, such as vacuum atomisation, countercurrent spray-drying etc. Such powders have a particle size of from 0.1 micrometres to 2 micrometres. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

The UV absorbers according to the present invention can also be used in specific carriers for cosmetics, for example in solid lipid nanoparticles (SLN) or in inert sol-gel microcapsules wherein the UV absorbers are encapsulated.

The cosmetic formulations or pharmaceutical compositions according to the present invention can also comprise one or more than one further UV filter as described in Tables 1-3.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, for example octyl methoxycinnamate, salicylic acid isooctyl ester etc. The UV absorber can be used, for example, without further treatment, or in the micronised state, or in the form of a powder.

Cosmetic or pharmaceutical preparations contain from 0.05% to 40% by weight, based on the total weight of the composition, of one UV absorber or a mixture of UV absorbers.

Preference is given to the use of mixing ratios of the UV absorber of formula (1) according to the present invention and optional further light-protective agents (as described in Tables 1-3) of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably approximately 50:50. Such mixtures can be used, inter alia, to improve solubility or increase UV absorption.

The UV absorbers of formula (1) according to the present invention or combinations of UV filters are useful for protecting skin, hair and/or natural or artificial hair colour.

TABLE 1

Suitable UV filter substances which can be additionally used with the UV absorbers according to the present invention
(The generic scope of the UV absorbers is described in the left-hand column; specific compounds are indicated in the right-hand column)

p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, US-A-5 338 539, US-A-5 518 713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in US-A-5 601 811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;

TABLE 1-continued

Suitable UV filter substances which can be additionally used with the UV absorbers according to the present invention
(The generic scope of the UV absorbers is described in the left-hand column; specific compounds are indicated in the right-hand column)

physical sunscreens, coated or not coated, such as titanium dioxide, zinc oxide, iron oxides, mica, MnO, $Fe_2O_3$, $Ce_2O_3$, $Al_2O_3$, $ZrO_2$ (surface coatings: polymethylmethacrylate, methicone (methylhydrogenpolysiloxane as described in CAS 9004-73-3), dimethicone, isopropyl titanium triisostearate (as described in CAS 61417-49-0), metal soaps such as magnesium stearate (as described in CAS 4086-70-8), perfluoroalcohol phosphate such as $C_9$-$C_{15}$ fluoroalcohol phosphate (as described in CAS 74499-44-8; JP 5-86984; JP 4-330007)). The primary particle size is, on average, 15 nm-35 nm and the particle size distribution is in the range 100 nm-300 nm.
aminohydroxy-benzophenone derivatives disclosed in DE 100 11 317, EP 1 133 980 and EP 1 046 391
phenyl-benzimidazole derivatives as disclosed in EP 1 167 358

TABLE 2

Suitable UV filter substances which can be additionally used with the UV absorbers according to the present invention

| | |
|---|---|
| DE 10331804 | T 1 p 4, T 2 + 3 p 5 |
| EP 613 893 | Ex 1-5 + 15, T 1, pp 6-8 |
| EP 1 000 950 | Comp. in Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 081 140 | Ex 1-9, pp 11-16 |
| EP 1 103 549 | Compounds 1-76, pp 39-51 |
| EP 1 108 712 | 4,5-Dimorph olino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 258 481 | Ex 1, pp 7, 8 |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 852 137 | T 2, pp 41-46 |
| EP 858 318 | T 1, p 6 |
| EP 863 145 | Ex 1-11, pp 12-18 |
| EP 895 776 | Comp. in rows 48-58, p 3; R 25 + 33, p 5 |
| EP 911 020 | T 2, p 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 967 200 | Ex 2; T 3-5, pp 17-20 |
| EP 969 004 | Ex 5, T 1, pp 6-8 |
| JP 2000319629 | CAS Reg Nos. 80142-49-0, 137215-83-9, 307947-82-6 |
| US 5 635 343 | all compounds on pp 5-10 |
| US 5 338 539 | Ex 1-9, pp 3 + 4 |
| US 5 346 691 | Ex 40, p 7; T 5, p 8 |
| US 5 801 244 | Ex 1-5, pp 6-7 |
| WO 0149686 | Ex 1-5, pp 16-21 |
| WO 0168047 | Tables on pp 85-96 |
| WO 0181297 | Ex 1-3, pp 9-11 |
| WO 0238537 | All compounds p 3, compounds on rows 1-10 p 4 |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations
T: Table,
R: row,
Comp: compound,
Ex: compound(s) of Patent Example,
p: page;
the generic scope of the UV absorbers is described in the left-hand column; specific compounds are indicated in the right-hand column)

TABLE 3

Suitable UV filter substances which can be additionally used with the UV absorbers according to the present invention
(The generic scope of the UV absorbers is described in the left-hand column; specific compounds are indicated in the right-hand column)

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-hydroxy-4-methoxybenzophenone | 131-57-7 |
| 7 | 2-hydroxy-4-methoxybenzophenone-5-sulfonic acid | 4065-45-6 |
| 8 | 2,2'-dihydroxy-4,4'-dimethoxybenzophenone | 131-54-4 |

TABLE 3-continued

Suitable UV filter substances which can be additionally used with the UV absorbers according to the present invention
(The generic scope of the UV absorbers is described in the left-hand column; specific compounds are indicated in the right-hand column)

| No. | Chemical Name | CAS No. |
|---|---|---|
| 9 | 2,2'-dihydroxy-4-methoxybenzophenone | 131-53-3 |
| 10 | alpha-(2-oxoborn-3-ylidene)toluene-4-sulfonic acid and its salts | 56039-58-8 |
| 11 | 1-[4-(1,1-dimethylethyl)phenyl]-3-(4-methoxyphenyl)propane-1,3-dione | 70356-09-1 |
| 12 | methyl N,N,N-trimethyl-4-[(4,7,7-trimethyl-3-oxobicyclo[2.2.1]hept-2-ylidene)methyl]anilinium sulphate; | 52793-97-2 |
| 22 | 3,3,5-trimethyl-cyclohexyl-2-hydroxy-benzoate | 118-56-9 |
| 23 | isopentyl p-methoxycinnamate | 71617-10-2 |
| 27 | menthyl o-aminobenzoate | 134-09-8 |
| 28 | menthyl salicylate | 89-46-3 |
| 29 | 2-ethylhexyl 2-cyano-3,3-diphenylacrylate | 6197-30-4 |
| 30 | 2-ethylhexyl 4-(dimethylamino)benzoate | 21245-02-3 |
| 31 | 2-ethylhexyl 4-methoxycinnamate | 5466-77-3 |
| 32 | 2-ethylhexyl salicylate | 118-60-5 |
| 33 | benzoic acid, 4,4',4''-(1,3,5-triazine-2,4,6-triyltriimino)tris-, tris(2-ethylhexyl) ester; 2,4,6-trianilino-(p-carbo-2'-ethylhexyl-1'-oxy)-1,3,5-triazine | 88122-99-0 |
| 34 | 4-aminobenzoic acid | 150-13-0 |
| 35 | benzoic acid, 4-amino-, ethyl ester, polymer with oxirane | 113010-52-9 |
| 38 | 2-phenyl-1H-benzimidazole-5-sulphonic acid | 27503-81-7 |
| 39 | 2-propenamide, N-[[4-[(4,7,7-trimethyl-3-oxobicyclo[2.2.1]hept-2-ylidene)methyl]phenyl]methyl]-, homopolymer | 147897-12-9 |
| 40 | triethanolamine salicylate | 2174-16-5 |
| 41 | 3,3'-(1,4-phenylenedimethylene)bis[7,7-dimethyl-2-oxo-bicyclo[2.2.1]heptane-1-methanesulfonic acid] | 90457-82-2 |
| 42 | titanium dioxide | 13463-67-7 |
| 44 | zinc oxide | 1314-13-2 |
| 45 | 2,2'-methylene-bis[6-(2H-benzotriazol-2-yl)-4-(1,1,3,3-tetramethyl-butyl)-phenol] | 103597-45-1 |
| 46 | 2,4-bis{[4-(2-ethylhexyloxy)-2-hydroxy]-phenyl}-6-(4-methoxy-phenyl)-(1,3,5)-triazine | 187393-00-6 |
| 47 | 1H-benzimidazole-4,6-disulfonic acid, 2,2'-(1,4-phenylene)bis-, disodium salt | 180898-37-7 |
| 48 | benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl) ester | 154702-15-5 |
| 49 | phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 50 | dimethicodiethylbenzalmalonate | 207574-74-1 |
| 51 | benzenesulfonic acid, 3-(2H-benzotriazol-2-yl)-4-hydroxy-5-(1-methylpropyl)-, monosodium salt | 92484-48-5 |
| 52 | benzoic acid, 2-[4-(diethylamino)-2-hydroxybenzoyl]-, hexyl ester | 302776-68-7 |
| 53 | 1-dodecanaminium, N-[3-[[4-(dimethylamino)benzoyl]amino]propyl]-N,N-dimethyl-, salt with 4-methylbenzenesulfonic acid (1:1) | 156679-41-3 |
| 54 | 1-propanaminium, N,N,N-trimethyl-3-[(1-oxo-3-phenyl-2-propenyl)-amino]-, chloride | 177190-98-6 |
| 55 | 1H-benzimidazole-4,6-disulfonic acid, 2,2'-(1,4-phenylene)bis- | 170864-82-1 |
| 56 | 1,3,5-triazine, 2,4,6-tris(4-methoxyphenyl)- | 7753-12-0 |
| 57 | 1,3,5-triazine, 2,4,6-tris[4-[(2-ethylhexyl)oxy]phenyl]- | 208114-14-1 |
| 58 | 1-propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-propenoic acid, 3-(1H-imidazol-4-yl)- | 104-98-3 |
| 60 | benzoic acid, 2-hydroxy-, [4-(1-methylethyl)phenyl]methyl ester | 94134-93-7 |
| 61 | 1,2,3-propanetriol, 1-(4-aminobenzoate) | 136-44-7 |
| 62 | benzeneacetic acid, 3,4-dimethoxy-α-oxo- | 4732-70-1 |
| 63 | 2-propenoic acid, 2-cyano-3,3-diphenyl-, ethyl ester | 5232-99-5 |
| 64 | anthranilic acid, p-menth-3-yl ester | 134-09-8 |
| 65 | 2,2'-bis(1,4-phenylene)-1H-benzimidazole-4,6-disulphonic acid monosodium salt or disodium phenyl dibenzimidazole tetrasulfonate or Neo-Heliopan AP | 349580-12-7 |

Suitable UV filter substances which can additionally be used with the UV absorbers according to the present invention are any UV-A and UV-B filter substances.

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also comprise one or one more additional compounds as described below.

Fatty Alcohols

Guerbet alcohols based on fatty alcohols having from 6 to 18, preferably from 8 to 10, carbon atoms, including cetyl alcohol, stearyl alcohol, cetearyl alcohol, oleyl alcohol, octyidodecanol, benzoates of $C_{12}$-$C_{15}$ alcohols, acetylated lanolin alcohol etc.

Esters of Fatty Acids

Esters of linear $C_6$-$C_{24}$ fatty acids with linear $C_3$-$C_{24}$ alcohols, esters of branched $C_6$-$C_{13}$carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropyl myristate, isopropyl palmitate, isopropyl stearate, isopropyl isostearate, isopropyl oleate, n-butyl stearate, n-hexyl laurate, n-decyl oleate, isooctyl stearate, isononyl stearate, isononyl isononanoate, 2-ethylhexyl palmitate, 2-hexyl laurate, 2-hexyldecyl stearate, 2-octyldodecyl palmitate, oleyl oleate, oleyl erucate, erucyl oleate, erucyl erucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate etc.

Other Adjuvants

Diethylhexyl 2,6-naphthalate, di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and iminodisuccinic acid salts [CAS 7408-20-0] or latex particles.

Natural or Synthetic Triglycerides, Including Glyceryl Esters and Derivatives

Di- or tri-glycerides, based on $C_8$-$C_{18}$ fatty acids, modified by reaction with other alcohols (caprylic/capric triglyceride, wheatgerm glycerides, etc.). Fatty acid esters of polyglycerol (polyglyceryl-n such as polyglyceryl-4 caprate, polyglyceryl-2 isostearate, etc.) or castor oil, hydrogenated vegetable oil, sweet almond oil, wheatgerm oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borage oil etc.

Waxes, including esters of long-chain acids and alcohols as well as compounds having wax-like properties, e.g. carnauba wax, beeswax (white or yellow), lanolin wax, candelilla wax, ozokerite, japan wax, paraffin wax, microcrystalline wax, ceresin, cetearyl ester wax, synthetic beeswax etc. Also, hydrophilic waxes such as cetearyl alcohol or partial glycerides.

Pearlescent Waxes

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules such as polydecenes and polybutene, hydrogenated polyisobutene, squalane, isohexadecane, isododecane and others of vegetable or animal origin.

Silicones or Siloxanes (Organo-substituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear poly-siloxanes, dimethicone (Dow Corning 200 fluid, Rhodia Mirasil DM), dimethiconol, cyclic silicone fluids, cyclopentasiloxane volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorohexane, dimethylcyclohexane, ethylcyclopentane, polyperfluoromethylisopropyl ether.

Emulsifiers

Any conventionally usable emulsifier can be used for the compositions. Emulsifier systems may comprise, for example: carboxylic acids and their salts: alkaline soaps of sodium, potassium and ammonium, metallic soaps of calcium or magnesium, organic-based soaps such as lauric, palmitic, stearic and oleic acid etc. Alkyl phosphates or phosphoric acid esters, acid phosphates, diethanolamine phosphate, potassium cetyl phosphate. Ethoxylated carboxylic acids or polyethylene glycol esters, PEG-n acylates. Linear fatty alcohols having from 8 to 22 carbon atoms, branched, from 2 to 30 mol of ethylene oxide and/or from 0 to 5 mol of propylene oxide with fatty acids having from 12 to 22 carbon atoms and with alkylphenols having from 8 to 15 carbon atoms in the alkyl group. Fatty alcohol polyglycol ethers such as laureth-n, ceteareth-n, steareth-n, oleth-n. Fatty acid polyglycol ethers such as PEG-n-stearate, PEG-n-oleate, PEG-n-cocoate. Monoglycerides and polyol esters. $C_{12}$-$C_{22}$ fatty acid mono- and di-esters of addition products of from 1 to 30 mol of ethylene oxide with polyols. Fatty acid and polyglycerol esters such as glycerol monostearate, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycol esters such as diethylene glycol monostearate, fatty acid and polyethylene glycol esters, fatty acid and saccharose esters such as sucrose esters, glycerol and saccharose esters such as sucrose glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquilsostearate, sorbitan, PEG-(6)-sorbitan isostearate, PEG-(10)-sorbitan laurate, PEG-17-sorbitan dioleate. Glucose derivatives, $C_8$-$C_{22}$alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcoholvcetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropylene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Amine derivatives, amine salts, ethoxylated amines, oxly amines with chains containing a heterocycle, such as alkyl imidazolines, pyridine derivatives, isoquinolines, cetylpyridinium chloride, cetylpyridinium bromide, quaternary ammonium such as cetyltrimethylammonium bromide (CTBA), stearylalkonium. Amide derivatives, alkanolamides such as acylamide DEA, ethoxylated amides such as PEG-n acylamide, oxydiamides. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethyl-ammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkyl peptides, lipoamino acids, self-emulsifying bases and the compounds as described in K. F. DePolo, A short textbook of cosmetology, Chapter 8, Table 8-7, p 250-251.

Non-ionic emulsifiers such as PEG-6 beeswax (and) PEG-6 stearate (and) polyglyceryl 2-isostearate [Apifac], glyceryl stearate (and) PEG-100 stearate. [Arlacel 165], PEG-5 glyceryl stearate [Arlatone 983 S], sorbitan oleate (and) polyglyceryl-3 ricinoleate [Arlacel 1689], sorbitan stearate and sucrose cocoate [Arlatone 2121], glyceryl stearate and laureth-23 [Cerasynth 945], cetearyl alcohol and Ceteth-20 [cetomacrogol wax], cetearyl alcohol and polysorbate 60 and PEG-150 and stearate-20 [polawax GP 200, polawax NF], cetearyl alcohol and cetearyl polyglucoside [Emulgade PL 1618], cetearyl alcohol and ceteareth-20 [Emulgade 1 OOONI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and steareth-7 and steareth-10 [emulsifying wax U.S.N.F], glyceryl stearate and PEG-75 stearate [Gelot 64], propylene glycol ceteth-3 acetate [Hetester PCS], propylene glycol isoceth-3 acetate [Hetester PHA], cetearyl alcohol and ceteth-12 and oleth-12 [Lanbritol Wax N21], PEG6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl alcohol and sodium cetearyl sulfate [Lanette N, Cutina LE, Crodacol GP], cetearyl alcohol and sodium lauryl sulfate [Lanette W], trilaneth-4 phosphate and glycol stearate and PEG-2 stearate [Sedefos 75], glyceryl stearate and sodium lauryl sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferred amount of such emulsifier systems may constitute 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition comprise, as further adjuvants and additives, mild surfactants, superfatting agents, consistency regulators, thickeners, polymers, stabilisers, biogenic active ingredients, deodorising active ingredients, antidandruff agents, film formers, swelling agents, further UV light-protective factors, antioxidants, hydrotropic agents, preservatives, insect repellents, self-tanning agents, solubilisers, perfume oils, colorants, bacteria-inhibiting agents and the like.

Superfatting Agents

Substances suitable for use as superfatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isothionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicon dioxide, magnesium silicates, aluminium silicates, polysaccharides or derivatives thereof for example hyaluronic acid, xanthan gum, guar-guar, agar-agar, alginates, carragheenan, gellan, pectins, or modified cellulose such as hydroxycellulose, hydroxypropyl methylcellulose. In addition polyacrylates or homopolymers of crosslinked acrylic acids and polyacrylamides, carbomers (Carbopol types 980, 981, 1382, ETD 2001, ETD2020, Ultrez 10) or the Salcare range such as Salcare SC80 (steareth-10 allyl ether/acrylate copolymer), Salcare SC81 (acrylate copolymer), Salcare SC91 and Salcare AST (sodium acrylate copolymer/PPG-1 trideceth-6), Sepigel 305 (polyacrylamide/laureth-7), Simulgel NS and Simulgel EG (hydroxyethyl acrylate/sodium acryloyldimethyl taurate copolymer), Stabilen 30 (acrylate/vinyl isodecanoate crosspolymer), Pemulen TR-1 (acrylate/$C_{10}$-$C_{30}$alkyl acrylate crosspolymer), Luvigel EM (sodium acrylate copolymer), Aculyn 28 (acrylate/beheneth-25 methacrylate copolymer) etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquat® (BASF), condensation products of polyglycols and amines, quatemised collagen polypeptides, for example lauryldimonium hydroxypropyl hydrolysed collagen (Lamequat®L/Grünau), quaternised wheat polypeptides, polyethyleneimine, cationic silicone polymers, for example amidomethicones, copolymers of adipic acid and dimethylaminohydroxypropyl diethylene-triamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleateAsobornyl acrylate copolymers, methyl vinyl ether/maleic anhydride copolymers and esters thereof, uncross-linked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinyl-pyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore, the polymers as described in EP 1 093 796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, anti-perspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-dandruff Agents

As anti-dandruff agents there may be used, for example, climbazole, octopirox and zinc pyrithione.

Film Formers

Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such anti-oxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, heptathionine sulfoximine), also (metal) chelating agents (e.g. hydroxy fatty acids, palmitic acid, phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. Further synthetic and natural antioxidants are listed e.g. in patent WO 0025731: structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propylene glycol, glycerol, ethylene glycol, ethylene glycol monoethyl ether, ethylene glycol monobutyl ether, propylene glycol monomethyl ether, propylene glycol monoethyl ether, propylene glycol monobutyl ether, diethylene glycol monomethyl ether; diethylene glycol monoethyl ether, diethylene glycol monobutyl ether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical-grade oligoglycerol mixtures having an intrinsic degree of condensation of from 1.5 to 10, for example technical-grade diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanol-amine or 2-amino-1,3-propanediol.

Preservatives and Bacteria-inhibiting Agents

Suitable preservatives include, for example, methyl, ethyl, propyl and butyl parabens, benzalkonium chloride, 2-bromo-2-nitro-propane-1,3-diol, dehydroacetic acid, diazolidinyl urea, 2-dichloro-benzyl alcohol, DMDM hydantoin, formaldehyde solution, methyldibromo-glutanitrile, phenoxyethanol, sodium hydroxymethylglycinate, imidazolidinyl urea, triclosan and further substance classes listed in the following reference: K. F. DePolo—A short textbook of cosmetology, Chapter 7, Table 7-2,7-3, 7-4 and 7-5, p 210-219.

Bacteria-inhibiting Agents

Typical examples of bacteria-inhibiting agents are preservatives that have a specific action against gram-positive bacteria, such as 2,4,4'-trichloro-2'-hydroxydiphenyl ether, chlor-hexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labdanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colorants

There may be used as colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colorants are usually used in concentrations of from 0.001 to 0.1% by weight, based on the total mixture.

Other Adjuvants

It is furthermore possible for the cosmetic preparations to comprise, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like styrene/acrylate copolymers, silica beads, spheroidal magnesium silicate, crosslinked polymethylmethacrylates (PMMA; Micopearl M305 Seppic), can maximize the UV protection of the sun products. Hollow-sphere additives (Sunspheres® ISP, Silica Shells Kobo.) deflect radiation and the effective path length of the photon is therefore increased (EP 0 893 119). Some beads, as mentioned previously, provide a soft feel during spreading. Moreover, the optical activity of such beads, e.g. Micropearl M305, can modulate skin-shine by eliminating reflection phenomena and may indirectly scatter the UV light.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hairstructuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:
in the form of liquid preparations as a W/O, OMw, OMw/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellent gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of special interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl dimethyl-2-hydroxyethylammonium chloride or Quaternium 80, is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80, is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacterio-static agents, perfumes, dyes, pigments, thickening agents, moisturising agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

Examples of Cosmetic and Pharmaceutical Preparations (X=Preferred Combinations)

| Ingredients | O/W systems: | | | | | | | |
|---|---|---|---|---|---|---|---|---|
| | 1 | 2 | 3 | 4 | 5 | 6 | 7 | 8 |
| Emulsifiers | | | | | | | | |
| Potassium cetyl phosphate 2%-5% | X | | | | | | | |
| Cetearyl alcohol/dicetyl phosphate/ceteth-10 phosphate 2%-6% | | X | | | | | | |
| Sodium stearyl phthalamate 1%-2% | | | X | | | | | |
| Cetearyl alcohol/behentrimonium methosulfate 1%-5% | | | | X | | | | |
| Quaternium-32 1%-5% | | | | | X | | | |
| Dimethicone copolyol/caprylic/capric triglyceride 1%-4% | | | | | | X | | |
| Steareth-2/steareth-21 2%-5% | | | | | | | X | |
| Polyglyceryl methyl glucose distearate 1%-4% | | | | | | | | X |
| Lipophilic emollient/dispersant oil 15%-20% | X | X | X | X | X | X | X | X |
| Fatty alcohols and/or waxes 1%-5% | X | X | X | X | X | X | X | X |
| Thickeners (water-swellable thickeners) 0.5%-1.5% | X | X | X | X | X | X | X | X |
| Preservatives 0.5%-1% | X | X | X | X | X | X | X | X |
| Chelating agents (such as EDTA) 0%-0.2% | X | X | X | X | X | X | X | X |
| Antioxidants 0.05%-0.2% | X | X | X | X | X | X | X | X |
| Water, deionised, q.s. 100% | X | X | X | X | X | X | X | X |
| Perfume oils 0.1%-0.4% | X | X | X | X | X | X | X | X |
| UV absorber according to the invention 0.1%-20% | X | X | X | X | X | X | X | X |
| UV absorber as described in Tables 1-3 0%-30% | X | X | X | X | X | X | X | X |

| Ingredients | W/O systems | | | | |
|---|---|---|---|---|---|
| | 1 | 2 | 3 | 4 | 5 |
| Emulsifiers | X | X | X | X | X |
| Polyglyceryl-2 dipolyhydroxystearate 2%-4% | X | X | X | X | X |
| PEG-30 dipolyhydroxystearate 2%-4% | | X | | | |
| Rapeseed oil sorbitol esters 1%-5% | | | X | | |
| PEG-45/dodecyl glycol copolymer 1%-5% | | | | X | |
| Sorbitan oleate/polycerol-3 ricinoleate 1%-5% | | | | | X |
| Lipophilic emollient/dispersant oil 10%-20% | X | X | X | X | X |
| Fatty alcohols and/or waxes 10%-15% | X | X | X | X | X |
| Electrolytes (NaCl, $MgSO_4$) 0.5%-1% | X | X | X | X | X |
| Polyol phase (propylene glycol, glycerol) 1%-8% | X | X | X | X | X |
| Preservatives 0.3%-0.8% | X | X | X | X | X |
| Perfume oils 0.1%-0.4% | X | X | X | X | X |
| Chelating agents (such as EDTA) 0%-0.2% | X | X | X | X | X |
| Antioxidants 0.05%-0.2% | X | X | X | X | X |
| Water, deionised, q.s. 100% | X | X | X | X | X |
| UV absorber according to the invention 0.1%-20% | X | X | X | X | X |
| UV absorber as described in Tables 1-3 0%-30% | X | X | X | X | X |

| W/silicone systems | | | | |
|---|---|---|---|---|
| Ingredients | 1 | 2 | 3 | 4 |
| Emulsifiers | | | | |
| Dimethicone copolyol/cyclomethicone 5%-10% | X | | X | |
| Laurylmethicone copolyol 5%-10% | | X | | X |
| Silicone phase | | | | |
| Cyclopentasiloxane 15%-25% | X | | | X |
| Dimethicone 15%-25% | | X | X | |
| Silicone elastomer | | | | |
| Dimethicone/vinyldimethicone crosspolymer 1%-10% | X | X | X | X |
| Humectant/polyols (propylene glycol, glycerol . . . ) 2%-8% | X | X | X | X |
| Chelating agents (such as EDTA) 0%-0.2% | X | X | X | X |
| Antioxidants 0.05%-0.2% | X | X | X | X |
| Preservatives 0.3%-0.8% | X | X | X | X |
| Perfume oils 0.1%-0.4% | X | X | X | X |
| Water, deionised q.s. 100% | X | X | X | X |
| UV absorber according to the invention 0.1%-20% | X | X | X | X |
| UV absorber as described in Tables 1-3 0%-30% | X | X | X | X |

| O1/W/O2 emulsions | | | | | | | | |
|---|---|---|---|---|---|---|---|---|
| Ingredients | 1 | 2 | 3 | 4 | 5 | 6 | 7 | 8 |
| Primary emulsion O1/W | | | | | | | | |
| PEG-60 hydrogenated castor oil 25% | X | | | X | X | | | X |
| Steareth-25 25% | | X | X | | | X | X | |
| Oil phase 75% | | | | | | | | |
| Fatty acid esters | X | | X | | | | | |
| Natural and synthetic triglycerides | | X | | X | | | | |
| Hydrocarbon oils | | | | | X | | X | |
| Silicone oils | | | | | | X | | X |
| Preservatives 0.3%-0.8% | X | X | X | X | X | X | X | X |
| Water, deionised, q.s. 100% | X | X | X | X | X | X | X | X |
| Non-ionic multifunctional W/O emulsifier 2%-5% | X | X | X | X | X | X | X | X |
| Waxes 1%-5% | X | X | X | X | X | X | X | X |
| Oil phase 20%-30% | X | X | X | X | X | X | X | X |
| Fatty acid esters | | | | | | | | |
| Natural and synthetic triglycerides | | | | | | | | |
| Hydrocarbon oils | | | | | | | | |
| Silicone oils | | | | | | | | |
| Primary emulsion O1/W 15% | X | X | X | X | X | X | X | |

| Multiple emulsions | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Primary emulsion W1/O | | | | | | | | | | | | |
| PEG-30 dipolyhydroxystearate 2%-6% | X | | | | | | | | | X | X | |
| Cetyl dimethicone copolyol 1%-3% | | X | | | | | | X | | | | |
| PEG-30 dipolyhydroxystearate/steareth-2/steareth-21 4%-6% | | | X | | | | X | | | | | |
| Polyglyceryl-2 dipolyhydroxystearate 1%-3% | | | | X | | | | X | | | | |
| Polyglyceryl-6 ricinoleate 1%-3% | | | | | X | X | | | | X | | |
| Oil phase 15%-30% | | | | | | | | | | | | |
| Fatty acid esters | X | X | X | X | X | | | | | X | X | |
| Natural and synthetic triglycerides | | | | | | X | X | X | X | X | X | |
| Hydrocarbon oils | X | X | X | X | | | | | | X | X | |
| Silicone oils | | | | | | X | X | X | X | X | X | |
| Preservatives 0.3%-0.8% | X | X | X | X | X | X | X | X | X | X | X | |
| Water, deionised, q.s. 100% | X | X | X | X | X | X | X | X | X | X | X | |
| Ionic monofunctional O/W emulsifiers | | | | | | | | | | | | |
| Sorbitan stearate/sucrose cocoate 3%-7% | X | | | | | | | X | | | X | |
| Sucrose laurate 3%-7% | | X | | | | X | | | X | | | |
| Poloxamer 407 3%-7% | | | X | | | | X | | | X | | |
| Polyoxyethylene (20) sorbate monoleate 3%-5% | | | | X | X | | | | | X | | |
| Primary emulsion W1/O 50% | X | X | X | X | X | X | X | X | X | X | X | |
| Thickeners (water-swellable polymers) 0.3%-1% | X | X | X | X | X | X | X | X | X | X | X | |
| Water, deionised, q.s. 100% | X | X | X | X | X | X | X | X | X | X | X | |
| Perfume oils 0.1%-0.4% | X | X | X | X | X | X | X | X | X | X | X | |
| UV absorber according to the invention 0.1%-20% | X | X | X | X | X | X | X | X | X | X | X | |
| UV absorber as described in Tables 1-3 0%-30% | X | X | X | X | X | X | X | X | X | X | X | |

-continued

O1/W/O2 emulsions

| Ingredients | 1 | 2 | 3 | 4 | 5 | 6 | 7 | 8 |
|---|---|---|---|---|---|---|---|---|
| Electrolytes (NaCl, MgSO$_4$) 0.1%-0.5% | X | X | X | X | X | X | X | X |
| Water, deionised, q.s. 100% | X | X | X | X | X | X | X | X |
| Perfume oils 0.1%-0.4% | X | X | X | X | X | X | X | X |
| UV absorber according to the invention 0.1%-20% | X | X | X | X | X | X | X | X |
| UV absorber as described in Tables 1-3 0%-30% | X | X | X | X | X | X | X | X |

Microemulsions

| Ingredients | 1 | 2 | 3 | 4 | 5 | 6 | 7 | 8 | 9 | 10 |
|---|---|---|---|---|---|---|---|---|---|---|
| Surfactants | | | | | | | | | | |
| PEG-8 caprylic/capric glycerides 10%-25% | X | | | X | X | | X | X | | |
| PPG-5-ceteth-20 10%-25% | | X | X | | | X | X | | | X |
| Co-surfactants | | | | | | | | | | |
| Polyglyceryl-6 isostearate 5%-15% | X | | X | | | | | | | |
| Polyglyceryl-3 diisostearate 5%-15% | | X | | X | | | | | | |
| Polyglyceryl-6 dioleate 5%-15% | | | | | X | X | | | | |
| PPG-10 cetyl ether 5%-15% | | | | | | X | X | | | |
| Ethoxydiglycol 5%-15% | | | | | | | | | X | X |
| Oil phase 10%-80% | X | X | X | X | X | X | X | X | X | X |
| Isostearyl benzoate | X | X | X | X | X | X | X | X | X | X |
| Isostearyl isostearate | X | X | X | X | X | X | X | X | X | X |
| PEG-7 glyceryl cocoate | X | X | X | X | X | X | X | X | X | X |
| Cyclomethicone | X | X | X | X | X | X | X | X | X | X |
| Polyalcohols/humectants 1%-10% | X | X | X | X | X | X | X | X | X | X |
| Preservatives 0.3-0.8% | X | X | X | X | X | X | X | X | X | X |
| Perfume oils 0.1%-0.4% | X | X | X | X | X | X | X | X | X | X |
| Water, deionised, q.s. 100% | X | X | X | X | X | X | X | X | X | X |
| UV absorber according to the invention 0.1%-20% | X | X | X | X | X | X | X | X | X | X |
| UV absorber as described in Tables 1-3 0%-30% | X | X | X | X | X | X | X | X | X | X |

O/W spray emulsions

| Ingredients | 1 | 2 | 3 | 4 | 5 | 6 |
|---|---|---|---|---|---|---|
| Emulsifiers | | | | | | |
| Alkyl phosphates 0.1%-5% | X | | | X | X | |
| Glucosidic derivatives 0.1%-5% | | X | X | | | X |
| Solubilisers | | | | | | |
| Ethoxylated glyceryl ethers 0.1%-1% | X | | X | | | |
| Polysorbates 0.1%-1% | | X | | X | | |
| Ethoxylated oleyl ethers 0.1%-1% | | | | | X | X |
| Film-forming agents | | | | | | |
| PVP/VA copolymer 1%-10% | X | | X | | X | |
| PVM/MA copolymer 1%-10% | | X | | X | | X |
| Oil phase 5%-20% | X | X | X | X | X | X |
| Natural oils (meadowfoam, jojoba, macadamia . . .) | X | X | X | X | X | X |
| Fatty acids esters | X | X | X | X | X | X |
| Mineral oils | X | X | X | X | X | X |
| Silicone oils | X | X | X | X | X | X |
| Alcohol 0%-50% | X | X | X | X | X | X |
| Thickeners 0.1%-0.5% | X | X | X | X | X | X |
| Polyacrylates | X | X | X | X | X | X |
| Aluminium/magnesium silicates | X | X | X | X | X | X |
| Gums | X | X | X | X | X | X |
| Neutralising agents 0%-1% | X | X | X | X | X | X |
| Polyalcohols/humectants 1%-5% | X | X | X | X | X | X |
| Chelating agents (such as EDTA) 0%-0.2% | X | X | X | X | X | X |
| Antioxidants 0.05%-0.2% | X | X | X | X | X | X |
| Water, deionised, q.s. 100% | X | X | X | X | X | X |
| Perfume oils 0.1%-0.5% | X | X | X | X | X | X |
| Preservatives 0.4%-1% | X | X | X | X | X | X |
| UV absorber according to the invention 0.1%-20% | X | X | X | X | X | X |
| UV absorber as described in Tables 1-3 0%-30% | X | X | X | X | X | X |

G - Aqueous

| Ingredients | 1 | 2 | 3 | 4 | 5 | 6 | 7 | 8 | 9 | 10 | 11 | 12 |
|---|---|---|---|---|---|---|---|---|---|---|---|---|
| Thickeners | | | | | | | | | | | | |
| Natural thickener 1%-5% | X | | | | X | X | | | | | | X |
| Semi-synthetic thickener 1%-5% | | X | | X | | | X | | | X | | |
| Synthetic thickener 0.3%-1.3% | | | X | X | | | | X | X | | | |
| Neutralising agents 0.5%-1.5% | X | X | X | X | X | X | X | X | X | X | X | X |
| Polyols - humectants 5%-50% | X | X | X | X | X | X | X | X | X | X | X | X |
| Film-forming agent/conditioner | | | | | | | | | | | | |
| Polyquaternium series 1%-5% | X | X | X | | | X | X | X | | | | |
| PVM/MA copolymer 1%-5% | | | | X | X | X | | | | X | X | X |

-continued

G - Aqueous

| Ingredients | 1 | 2 | 3 | 4 | 5 | 6 | 7 | 8 | 9 | 10 | 11 | 12 |
|---|---|---|---|---|---|---|---|---|---|---|---|---|
| Preservatives 0.5%-1% | X | X | X | X | X | X | X | X | X | X | X | X |
| Chelating Agents (as EDTA) <0.1% | X | X | X | X | X | X | X | X | X | X | X | X |
| Water, deionised, q.s. 100% | X | X | X | X | X | X | X | X | X | X | X | X |
| Perfume oils 0.05%-0.4% | X | X | X | X | X | X | X | X | X | X | X | X |
| Solubilisers | | | | | | | | | | | | |
| Ethoxylated glyceryl ethers 0.1%-5% | X | X | X | | | | | | | | | |
| Polysorbates 0.1%-5% | | | | X | X | X | | | | | | |
| Ethoxylated oleyl ethers 0.1%-5% | | | | | | | X | X | X | X | X | X |
| UV absorber according to the invention 0.1%-20% | X | X | X | X | X | X | X | X | X | X | X | X |
| UV absorber as described in Tables 1-3 0%-30% | X | X | X | X | X | X | X | X | X | X | X | X |

Oleogels

| Ingredients | 1 | 2 | 3 | 4 | 5 | 6 | 7 | 8 | 9 | 10 |
|---|---|---|---|---|---|---|---|---|---|---|
| Thickeners | | | | | | | | | | |
| Hydrogenated lecithin 1%-10% | X | | | | | | | | | X |
| Silica dimethyl silylate 1%-10% | | X | | | | | | X | | |
| Silica 1%-5% | | | X | | | | X | | | |
| $C_{24-28}$ Alkyl dimethicone 1%-5% | | | | X | | | X | | | |
| Aluminium or magnesium stearate 1%-5% | | | | | X | X | | | | |
| Polyols - humectants 5%-70% | X | X | X | X | X | X | X | X | X | |
| Oil phase 20%-90% | | | | | | | | | | |
| Dicaprylyl ether | X | | | | | X | X | | | |
| Phenyl trimethicone | | X | | | | | X | | | |
| Hydrogenated polyisobutene | | X | | | | | | | | |
| Isopropyl isostearate | | | | X | | | | X | | |
| Oleogel base (mineral oil and hydrogenated butylene/ethylene or ethylene/propylene styrene copolymer) | | | | | X | | | | X | |
| Silicone wax 1%-10% | X | X | X | X | X | X | X | X | X | |
| Dimethiconol behenate | X | X | X | X | X | X | X | X | X | |
| Dimethiconol stearate | X | X | X | X | X | X | X | X | X | |
| Perfume oils 0.1%-0.5% | X | X | X | X | X | X | X | X | X | |
| Antioxidants 0.05%-0.2% | X | X | X | X | X | X | X | X | X | |
| UV absorber according to the invention 0.1%-20% | X | X | X | X | X | X | X | X | X | |
| UV absorber as described in Tables 1-3 0%-30% | X | X | X | X | X | X | X | X | X | |

Light/dry cosmetic oils

| Ingredients | 1 | 2 | 3 | 4 |
|---|---|---|---|---|
| Lipophilic base | | | | |
| Hydrocarbon oils 30%-70% | X | | | X |
| Fatty acid esters, branched or unbranched 10%-50% | | X | X | |
| Light-feel agent | | | | |
| Silicones/siloxanes 0%-10% | X | | X | |
| Perfluorinated oils and perfluoroethers 0%-10% | | X | | X |
| Viscosifying agents 0%-10% | X | X | X | X |
| Waxes | | | | |
| Esters of long-chain acids and alcohols 0%-2% | X | X | X | X |
| Antioxidants 0.1%-1% | X | X | X | X |
| Solubilisers/dispersing agents 0%-5% | X | X | X | X |
| Perfume oils 0.1%-0.5% | X | X | X | X |
| UV absorber according to the invention 0.1%-20% | X | X | X | X |
| UV absorber as described in Tables 1-3 0%-30% | X | X | X | X |

Foaming/mousse products

| Ingredients | |
|---|---|
| SD Alcohol 40 0%-8% | X |
| Propellant 8%-15% | X |
| Nonionic emulsifier/surfactant 0.5%-3% | X |
| Corrosion Inhibitor 0%-1% | X |
| Perfume oils 0.1%-0.5% | X |
| Preservatives 0.1%-1% | X |
| Miscellaneous 0%-1% | X |
| UV absorber according to the invention 0.1%-20% | X |
| UV absorber as described in Tables 1-3 0%-30% | X |

Stick products

| Ingredients | |
|---|---|
| Waxes 15%-30% | X |
| Natural and silicone oils 20%-75% | X |
| Lanolin derivatives 5%->50% | X |
| Esters of lanolin | x |

-continued

Stick products

| Ingredients | |
|---|---|
| Acetylated lanolin | x |
| Lanolin oil | x |
| Colorants and pigments 10%-15% | X |
| Antioxidants 0.1%-0.8% | X |
| Perfume oils 0.1%-2% | X |
| Preservatives 0.1%-0.7% | X |
| UV absorber according to the invention 0.1%-20% | X |
| UV absorber as described in Tables 1-3 0%-30% | X |

Liquid and compact

| Ingredients | 1 | 2 |
|---|---|---|
| Liquid foundation | | |
| Powder phase 10%-15% | X | |
| Oil phase 30%-40%; 75% (only for anhydrous form) | X | |
| Thickener/suspending agents 1%-5% | X | |
| Film-forming polymers 1%-2% | X | |
| Antioxidants 0.1%-1% | X | |
| Perfume oils 0.1%-0.5% | X | |
| Preservatives 0.1%-0.8% | X | |
| Water, deionised, q.s. 100% | X | |
| Compact powder | | |
| Powder phase 15%-50% | | X |
| Oil phase 15%-50% | | X |
| Polyol phase 5%-15% | | X |
| Antioxidants 0.1%-1% | | X |
| Perfume oils 0.1%-0.5% | | X |
| Preservatives 0.1%-0.8% | | X |
| For the two product forms | | |
| UV absorber according to the invention 0.1%-20% | X | X |
| UV absorber as described in Tables 1-3 0%-30% | X | X |

Conditioning Shampoos

| Ingredients | 1 |
|---|---|
| Primary surfactants (listed previously) 5%-10% | X |
| Secondary surfactants (listed previously) 5%-15% | X |
| Foam stabilisers (listed previously) 0%-5% | X |
| Water, deionised, 40%-70% | X |
| Actives 0-10% | X |
| Conditioners | x |
| Refatting agents | x |
| Moisturising agents | x |

Conditioning Shampoos

| Ingredients | 1 |
|---|---|
| Thickeners/rheology modifiers 0%-3% | X |
| Humectants 0%-2% | X |
| pH-adjusting agents 0%-1% | X |
| Preservatives 0.05%-1% | X |
| Perfume oils 0.1%-1% | X |
| Antioxidants 0.05%-0.20% | X |
| Chelating agents (EDTA) 0%-0.2% | X |
| Opacifying agents 0%-2% | X |
| UV absorber according to the invention 0.1%-20% | X |
| UV absorber as described in Tables 1-3 0%-30% | X |

In the Examples that follow, percentages are based on weight.

PREPARATION EXAMPLES

Example 1

Preparation of the Compound of Formula

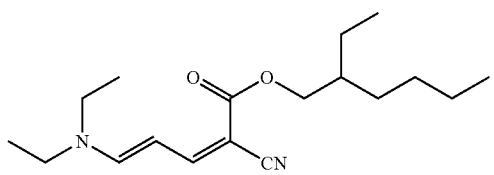

(101)

N-(3-Anilino-allylidene)-aniline (4.5 g, 0.02 mol) and cyanoacetic acid 2-ethylhexyl ester (4.2 g, 0.021 mol) are stirred in 10 ml of acetanhydride for 2 hours at 85-90° C. After removing the excess of acetanhydride in vacuo, the reaction batch is poured onto ice, and the resulting precipitate is filtered off and washed with copious amounts of water. After drying in vacuo at 60° C., the intermediate product is taken up in 10 ml of dry ethanol, and diethylamine (3.1 g, 0.042 mol) is added. The reaction mixture is stirred for 2 hours at 50-55° C. The ethanol and the excess of amine are then distilled off in vacuo. The residue, in a mixture of toluene and acetone (9.5: 0.5), is subjected to fractionated filtration over silica gel 60 from Merck and isolated. The pure product is dried under a high vacuum at 60° C. Yield: 4.5 g (73.5% of theory).

Example 2

Preparation of the Compound of Formula

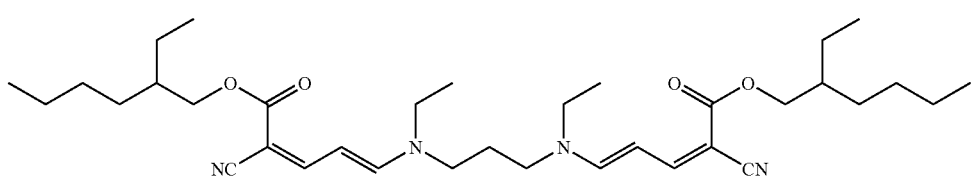

(102)

N-(3-Anilino-allylidene)-aniline (4.5 g, 0.02 mol) and cyanoacetic acid 2-ethylhexyl ester (4.2 g, 0.021 mol) are stirred in 10 ml of acetanhydride for 2 hours at 85-90° C. After removing the excess of acetanhydride in vacuo, the reaction batch is poured onto ice, and the resulting precipitate is filtered off and washed with copious amounts of water. After drying in vacuo at 60° C., the intermediate product is taken up in 10 ml of dry ethanol, and diethyl-1,3-propanediamine (1.3 g, 0.01 mol) is added.

The reaction mixture is stirred for 2 hours at 50° C. The ethanol is then distilled off, and the residue, in a mixture of toluene and acetone (9:1), is subjected to fractionated filtration over silica gel 60 from Merck and isolated. The pure product is then dried in vacuo at 60° C. Yield: 4.4 g (73% of theory).

Example 3

Preparation of the Compound of Formula

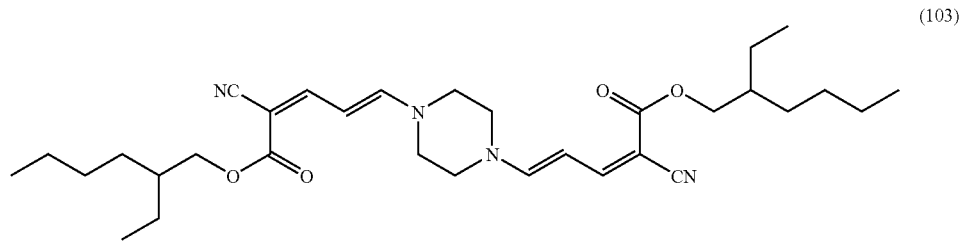

(103)

N-(3-Anilino-allylidene)-aniline (4.5 g, 0.02 mol) and cyanoacetic acid 2-ethylhexyl ester (4.2 g, 0.021 mol) are stirred in 10 ml of acetanhydride for 2 hours at 85-90° C. After removing the excess of acetanhydride in vacuo, the reaction batch is poured onto ice, and the resulting precipitate is filtered off and washed with copious amounts of water. After drying in vacuo at 60° C., the intermediate product is taken up in 10 ml of dry ethanol, and piperazine (0.8 g, 0.01 mol) is added. After stirring for 2 hours at 50-55° C., the ethanol is distilled off in vacuo. Subsequent column chromatography over silica gel 60 from Merck using a mixture of toluene and acetone (9:1) yields the pure product, which is dried in vacuo at 60° C. Yield: 3.9 g (69% of theory).

APPLICATION EXAMPLES

Example 4

O/W Emulsion

| (A): | |
|---|---|
| UV absorber of formula (101) | 3 g |
| sesame oil | 10 g |
| glyceryl stearate | 4 g |
| stearic acid | 1 g |
| cetyl alcohol | 0.5 g |
| polysorbate 20 | 0.2 g |

| (B): | |
|---|---|
| propylene glycol | 4 g |
| propylparaben | 0.05 g |
| methylparaben | 0.15 g |
| triethanolamine | 0.1 g |
| carbomer 934 | 0.1 g |
| water | ad 100 ml |

Preparation of the Emulsion

Phase (A):

Firstly, the UV absorber is dissolved in sesame oil. The other components of (A) are added thereto and combined.

Phase (B):

Propylparaben and methylparaben are dissolved in propylene glycol. 60 ml of water are then added, heating to 70° C. is carried out and then carbomer 934 is emulsified therein.

Emulsion:

(A) is slowly added to (B) with vigorous application of mechanical energy. The volume is adjusted to 100 ml by the addition of water.

Example 5

Daily Care Cream, Type O/W

| | INCI name | % w/w (as used) |
|---|---|---|
| Part A | Glyceryl stearate (and) cetearyl alcohol (and) cetyl palmitate (and) cocoglycerides | 4.0 |
| | Ceteareth-12 | 4.0 |
| | Cetearyl alcohol | 2.0 |
| | Dicaprylyl ether | 4.5 |
| | Ethylhexyl stearate | 4.0 |
| | Hexyl laurate | 3.5 |
| | Ethylhexyl triazone | 1.0 |
| | Benzylidene malonate polysiloxane | 2.0 |
| | HDI/trimethylol hexyl-lactone crosspolymer (and) silica | 5.0 |
| | Stearyl dimethicone | 1.0 |
| | Dimethicone | 2.0 |
| | Cetyl alcohol | 0.8 |
| | compound of formula (101) | 2.0 |
| Part B | Water | q.s. to 100 |
| | Water (and) scleroglucan (and) phenoxyethanol | 2.0 |
| | Glycerol | 2.0 |
| Part C | Steareth-10 allyl ether/acrylate copolymer | 0.45 |
| | Phenoxyethanol (and) methylparaben (and) ethylparaben (and) butylparaben (and) propylparaben (and) isobutylparaben | 0.7 |

-continued

| | INCI name | % w/w (as used) |
|---|---|---|
| Part D | Aqua (and) tocopheryl acetate (and) caprylic/capric triglyceride (and) polysorbate 80 (and) lecithin | 4.0 |
| Part E | Water (and) sodium hydroxide | q.s. |
| | Fragrance | q.s. |

Preparation Procedure:

Part A and part B are heated separately to 80° C. Part A is poured into part B, whilst stirring continuously. Afterwards the mixture is homogenized with an Ultra Turrax at 11 000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

Example 6

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (101a) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. The mixture is cooled to 60° C. and part C and part D are incorporated. The mixture Is homogenised again for a short time (5 sec./11 000 rpm) and further cooled, with moderate stirring. At room temperature, the pH is adjusted with sodium hydroxide solution to between 5.5 and 6.0. Finally, fragrance is added.

Example 7

Daily Care UV-protection Lotion

| | INCI name | % w/w (as used) |
|---|---|---|
| Part A | Oleth-3 phosphate | 0.6 |
| | Steareth-21 | 2.5 |
| | Steareth-2 | 1.0 |
| | Cetyl alcohol | 0.8 |
| | Stearyl alcohol | 1.5 |
| | Tribehenin | 0.8 |
| | Isohexadecane | 8.0 |
| | compound of formula (101) | 5.0 |
| Part B | Water | q.s. to 100 |
| | Glycerol | 2.0 |
| | Methylene bis-benzotriazolyl tetramethylbutylphenol (and) aqua (and) decyl glucoside (and) propylene glycol (and) xanthan gum | 3.0 |
| | Disodium EDTA | 0.1 |
| Part C | Water | 20.0 |
| | Diazolidinyl urea (and) iodopropynyl butylcarbamate | 0.15 |
| | Propylene glycol | 4.0 |
| Part D | Sodium acrylate copolymer (and) liquid paraffin (and) PPG-1 trideceth-6 | 1.5 |
| | Cyclopentasiloxane | 4.5 |
| | PEG-12 dimethicone | 2.0 |
| | Tocopheryl acetate | 0.45 |
| | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11 000 rpm for 30 sec. Allow to cool to 65° C. and incorporate SALCARE SC91. At a temperature below 50° C., add part C. At 35° C. or below, incorporate vitamin E acetate and subsequently adjust the pH with citric acid. At room temperature, add part E.

Example 8

Sun-protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (101) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. The mixture is cooled to 60° C., and part C and part D are incorporated. The mixture is homogenised again for a short time (5 sec./11 000 rpm). After further cooling, with moderate stirring, the pH is adjusted with sodium hydroxide at room temperature. A solution between pH 5.50 and 6.00 is obtained. Finally, fragrance is added.

Example 9

Sun-protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of formula (101) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. After cooling 60° C., part C and part D are incorporated. The mixture is homogenised again for a short time (5 sec./11 000 rpm). After further cooling, with moderate stirring, the pH is adjusted at room temperature with sodium hydroxide solution to between 5.50 and 6.00. Finally, fragrance is added.

Example 10

Sun-protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of compound of formula (101) (50%) and benzylidene camphor, CAS Reg. No. 36861-47-9 (50%) | 2.0 |
| | Ethylhexyl methoxycinnamate | 5.0 |
| | Cetyl alcohol | 0.7 |

-continued

| | INCI name | % w/w (as used) |
|---|---|---|
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. After cooling to 60° C., part C and part D are incorporated. The mixture is homogenised again for a short time (5 sec./11 000 rpm). After further cooling, with moderate stirring, the pH is adjusted at room temperature with sodium hydroxide. A solution between pH 5.50 and 6.00 is obtained. Finally, fragrance is added.

What is claimed is:

1. A method of protecting human and animal hair or skin from UV radiation, which comprises contacting said hair or skin with an effective UV-protective amount of a compound of formula

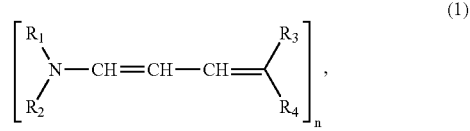

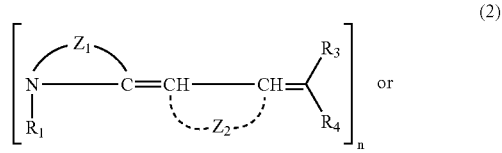

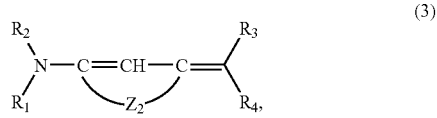

wherein $R_1$ and $R_2$ are each independently of the other hydrogen; $C_1$-$C_{22}$alkyl; cyclo-$C_3$-$C_8$alkyl; or unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is uninterrupted or interrupted by —O— or by —NH—;

$R_3$ is a cyano group; —$COOR_5$; —$CONHR_5$; —$COR_5$; —$SO_2R_5$; or —$CONR_1R_5$;

$R_4$ is a cyano group; —$COOR_6$; —$CONHR_6$; —$COR_6$; —$SO_2R_6$; or —$CONR_2R_6$;

$R_5$ and $R_6$ are each independently of the other $C_1$-$C_{22}$alkyl; cyclo-$C_3$-$C_8$alkyl; or unsubstituted or $C_1$-$C_6$alkyl-substituted $C_6$-$C_{20}$aryl;

or $R_3$ and $R_4$ together or $R_5$ and $R_6$ together form a 5- to 7-membered, monocyclic, carbocyclic or heterocyclic ring;

$Z_1$ and $Z_2$ are each independently of the other a —$(CH_2)_l$— group which is uninterrupted or interrupted by —O—, —S—, or by —$NR_7$—, and/or is unsubstituted or substituted by $C_1$-$C_6$alkyl;

$R_7$ is $C_1$-$C_5$alkyl;

l is a number from 1 to 4;

m is a number from 1 to 7;

n is a number from 1 to 4;

when n=2, $R_1$, $R_5$ or $R_6$ is a bivalent alkyl group; or $R_1$ and $R_2$ together with the 2 nitrogen atoms linking them form a —$(CH_2)_m$— ring;

when n=3, $R_1$, $R_5$ or $R_6$ is a trivalent alkyl group;

when n=4, $R_1$, $R_5$ or $R_6$ is a tetravalent alkyl group; and $R_1$ and $R_2$ in formula (1) are not simultaneously hydrogen.

2. A method according to claim 1, relating to a compound of formula (1) or (2a)

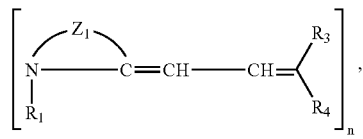

wherein $R_1$ and $R_2$ are each independently of the other hydrogen; $C_1$-$C_{22}$alkyl; or unsubstituted or $C_1$-$C_5$alkyl- or $C_1$-$C_5$alkoxy-substituted $C_6$-$C_{20}$aryl; or $R_1$ and $R_2$ together with the nitrogen atom linking them form a —$(CH_2)_m$— ring which is uninterrupted or interrupted by —O— or by —NH—;

$R_3$ is a cyano group; —$COOR_5$; —$CONHR_5$; —$COR_5$; or —$SO_2R_5$;

$R_4$ is a cyano group; —$COOR_6$; —$CONHR_6$; —$COR_6$; or —$SO_2R_6$;

$R_5$ and $R_6$ are each independently of the other $C_1$-$C_{22}$alkyl; or unsubstituted or $C_1$-$C_5$alkyl-substituted $C_6$-$C_{20}$aryl; or $R_5$ and $R_6$ together form a 5- to 7-membered, monocyclic, carbocyclic or heterocyclic ring;

$Z_1$ and $Z_2$ are each independently of the other a —$(CH_2)_l$— group which is uninterrupted or interrupted by —O—, —S—, or by —$NR_7$—, and/or is unsubstituted or substituted by $C_1$-$C_5$alkyl;

$R_7$ is $C_1$-$C_5$alkyl;

l is a number from 1 to 4;

m is a number from 1 to 7;

n is a number from 1 to 4;

when n=2, $R_1$, $R_5$ or $R_6$ is a bivalent alkyl group; or $R_1$ and $R_2$ together with the 2 nitrogen atoms linking them form a —$(CH_2)_m$— ring;

when n=3, $R_1$, $R_5$ or $R_6$ is a trivalent alkyl group;

when n=4, $R_1$, $R_5$ or $R_6$ is a tetravalent alkyl group; and $R_1$ and $R_2$ in formula (1) are not simultaneously hydrogen.

3. A method according to claim 1, wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is a cyano group; —$COOR_5$; —$CONHR_5$; —$COR_5$; or —$SO_2R_5$;

$R_4$ is a cyano group; —$COOR_6$; —$CONHR_6$; —$COR_6$; or —$SO_2R_6$;

$R_5$ and $R_6$ are each independently of the other $C_1$-$C_{22}$alkyl; or $C_6$-$C_{20}$aryl; and Z is as defined in claim 1.

4. A method Use according to claim 1, wherein $R_3$ is a cyano group; and $R_4$ is —$CONHR_6$; and $R_6$ is $C_1$-$C_{22}$alkyl; or $C_6$-$C_{20}$aryl.

5. A method according to claim 1, wherein $R_6$ is $C_4$-$C_{20}$alkyl.

6. A method according to claim 1, wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is —$COOR_5$;

$R_4$ is a cyano group; —$COOR_6$; or —$SO_2R_6$;

$R_5$ and $R_6$ are each independently of the other $C_1$-$C_{22}$alkyl; or $C_6$-$C_{20}$aryl; and m is from 1 to 7.

7. A method according to claim 6, wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is —$COOR_5$;

$R_4$ is —$COOR_6$;

$R_5$ and $R_6$ are each independently of the other $C_1$-$C_{22}$alkyl; or $C_6$-$C_{20}$aryl; and m is from 1 to 7.

8. A method according to claim 6, wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is —$COOR_5$;

$R_4$ is a cyano group;

$R_5$ is $C_1$-$C_{22}$alkyl; or $C_6$-$C_{20}$aryl; and m is from 1 to 7.

9. A method according to claim 6, wherein $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;

$R_3$ is —$COOR_5$;

$R_4$ is —$SO_2R_6$;

$R_5$ and $R_6$ are each independently of the other $C_1$-$C_{22}$alkyl; or $C_6$-$C_{20}$aryl; and m is from 1 to 7.

10. A method according to claim 1, which comprises using a compound of formula

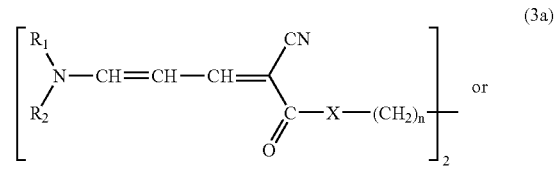

-continued

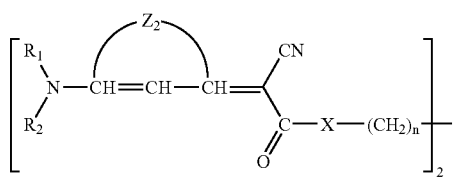

wherein
- $R_1$ and $R_2$ are each independently of the other $C_1$-$C_{22}$alkyl; or $R_1$ and $R_2$ together with the 2 nitrogen atoms linking them form a —$(CH_2)_m$— ring;
- X is —O—; or —NH—;
- $Z_2$ is a —$(CH_2)_l$— group which is uninterrupted or interrupted by —O—, —S—, or by —$NR_7$—, and/or is unsubstituted or substituted by $C_1$-$C_6$alkyl; and
- n is a number from 1 to 3.

11. A method according to claim 10, wherein
$R_1$ and $R_2$ are each independently of the other $C_1$-$C_{22}$alkyl; or $R_1$ and $R_2$ together with the nitrogen atom linking them form the radical

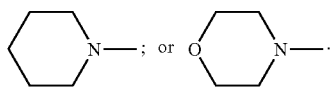

12. A method according to claim 1, which comprises using a compound of formula

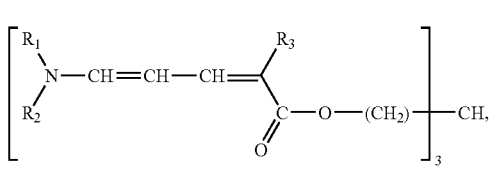

wherein
- $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
- $R_3$ is a cyano group; —$COOR_5$; —$CONHR_5$; —$COR_5$; or —$SO_2R_5$; and
- $R_5$ and $R_6$ are each independently of the other $C_1$-$C_{22}$alkyl; or $C_6$-$C_{20}$aryl.

13. A method according to claim 12, wherein
$R_1$ and $R_2$ are each independently of the other $C_1$-$C_{22}$alkyl; or $R_1$ and $R_2$ together with the nitrogen atom linking them form the radical

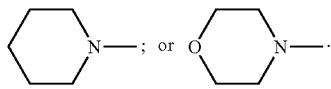

14. A method according to claim 1, which comprises using a compound of formula

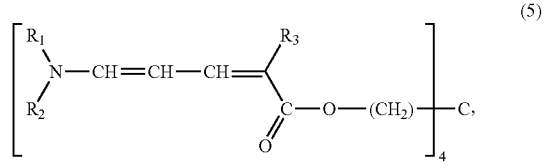

wherein
- $R_1$ and $R_2$ are each independently of the other $C_1$-$C_{22}$alkyl; or $R_1$ and $R_2$ together with the nitrogen atom linking them form a —$(CH_2)_m$— ring which is uninterrupted or interrupted by —O— or by —NH—;
- $R_3$ is a cyano group; —$COOR_5$; —$CONHR_5$; —$COR_5$; or —$SO_2R_5$; and
- $R_5$ is $C_1$-$C_{22}$alkyl; or $C_6$-$C_{20}$aryl.

15. A method according to claim 14, wherein
$R_1$ and $R_2$ are each independently of the other $C_1$-$C_{22}$alkyl; or $R_1$ and $R_2$ together with the nitrogen atom linking them form the radical

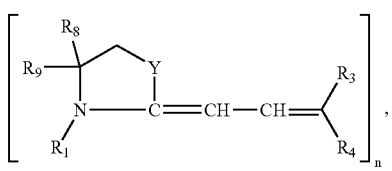

16. A method according to claim 1, wherein
$Z_1$ or $Z_2$ is an atom grouping which results in the formation of an oxazolidine ring, a pyrrolidine ring or a thiazolidine ring.

17. A method according to claim 16, wherein the compound corresponds to formula $$\left[ \begin{array}{c} R_8 \\ R_9 \end{array} \underset{R_1}{\overset{Y}{\underset{N}{\bigvee}}} C=CH-CH \underset{R_4}{\overset{R_3}{=}} \right]_n, \quad (2b)$$

wherein
- $R_8$ and $R_9$ are each independently of the other hydrogen; or $C_1$-$C_5$alkyl;
- Y is —O—; —S—; or —$CH_2$—;
- $R_1$ is hydrogen; $C_1$-$C_{22}$alkyl; cyclo-$C_3$-$C_8$alkyl; or unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is uninterrupted or interrupted by —O— or by —NH—;
- $R_3$ is a cyano group; —$COOR_5$; —$CONHR_5$; —$COR_5$; or —$SO_2R_5$; —$CONR_1R_5$;
- $R_4$ is a cyano group; —$COOR_6$; —$CONHR_6$; —$COR_6$; or —$SO_2R_6$; —$CONR_2R_6$;
- $R_5$ and $R_6$ are each independently of the other $C_1$-$C_{22}$alkyl; cyclo-$C_3$-$C_8$alkyl; or unsubstituted or $C_1$-$C_6$alkyl-substituted $C_6$-$C_{20}$aryl;
- or $R_3$ and $R_4$ together or $R_5$ and $R_6$ together form a 5- to 7-membered, monocyclic, carbocyclic or heterocyclic ring; and
- n is a number from 1 to 4.

18. A method according to claim 17, wherein
$R_1$ is $C_1$-$C_{12}$alkyl;
$R_3$ is a cyano group; —COOR$_5$; —COR$_5$; or —SO$_2$R$_5$;
$R_4$ is —COR$_6$; or —COOR$_6$;
$R_5$ and $R_6$ are each independently of the other unsubstituted or $C_1$-$C_5$alkyl- or $C_1$-$C_5$alkoxy-substituted $C_6$-$C_{20}$aryl.

19. A cosmetic preparation comprising at least one or more compounds of formula (1) or (2) according to claim 1 with cosmetically acceptable carriers or adjuvants.

* * * * *